United States Patent [19]

Inoue et al.

[11] Patent Number: 5,843,951
[45] Date of Patent: Dec. 1, 1998

[54] ANALGESIC COMPOSITION OF PYRAZOLO (1,5-A) PYRIMIDINES

[75] Inventors: Makoto Inoue; Takashi Okamura; Yasuo Shoji; Kinji Hashimoto, all of Naruto; Masayuki Ohara, Tokushima-ken; Tsuneo Yasuda, Naruto, all of Japan

[73] Assignee: Otsuka Pharmaceutical Factory Inc., Tokushima, Japan

[21] Appl. No.: 836,822

[22] PCT Filed: Sep. 24, 1996

[86] PCT No.: PCT/JP96/02759

§ 371 Date: May 21, 1997

§ 102(e) Date: May 21, 1997

[87] PCT Pub. No.: WO97/11946

PCT Pub. Date: Apr. 3, 1997

[30] Foreign Application Priority Data

Sep. 28, 1995 [JP] Japan .................................. 7-289096

[51] Int. Cl.$^6$ ................................................. A61K 31/505
[52] U.S. Cl. ............................................................ 514/258
[58] Field of Search ............................................. 514/258

[56] References Cited

FOREIGN PATENT DOCUMENTS

| | | |
|---|---|---|
| 0714898 | 6/1996 | European Pat. Off. |
| 2236987 | 3/1973 | Germany . |
| 2257547 | 6/1973 | Germany . |
| 5125079 | 5/1993 | Japan . |
| 961907 | 6/1964 | United Kingdom . |
| 1011048 | 11/1965 | United Kingdom . |

OTHER PUBLICATIONS

*Journal of Medicinal Chemistry*, Dec. 1983, vol. 26, No. 12, pp. 1706–1709, Auzzi, et al., "2–Phenylpyrazolo[1,5–a]pyrimidin–7–ones. A New Class of Nonsteroidal Antiinflammatory Drugs Devoid of Ulcerogenic Activity".

*Journal of Pharmaceutical Sciences*, May 1983, vol. 82, No. 5, pp. 480–486, Bruni, et al., "Synthesis and Study of the Anti–inflammatory Properties of Some Pyrazolo[1,5–a]pyrimidine Derivatives".

*Pharmacological Research Communications*, 1986, vol. 18, No. 3, pp. 241–256, Pirisino, et al., "Pharmacological Activity of FPP028 (2–Phenylpirazolo–4–Ethyl–4,7–Dihydro[1,5a]Pirimidin–7–One) A Non–Steroid Anti–inflammatory Agent".

Pirisino et al., Chemical Abstracts, vol. 95, No. 15, Oct. 12, 1981, abstract No. 125870b.

Otsuka Pharmaceutical Factory, Patent Abstract of Japan, vol. 096, No. 005, May 31, 1996, referencing JP 08 003167.

Otsuka Pharmaceutical Factory, Patent Abstract of Japan, vol. 017, No. 291, Jun. 4, 1993 referencing JP 05 017470.

Takamizawa et al., Chemical Abstracts, vol. 72, No. 15, Apr. 13, 1970, abstract No. 79088c.

Vettori et al., Chemical Abstracts, vol. 95, No. 15, Oct. 12, 1981, abstract No. 132797m.

Otsuka Pharmaceutical Factory, Patent Abstract of Japan, vol. 96, No. 003, Mar. 29, 1996 referencing JP 07 309872.

*Primary Examiner*—William R. A. Jarvis
*Attorney, Agent, or Firm*—Sughrue, Mion, Zinn, Macpeak & Seas, PLLC

[57] ABSTRACT

The invention provides an analgesic composition containing as an active ingredient a specific pyrimidine derivative represented by one of the follwing formulas (1) to (3):

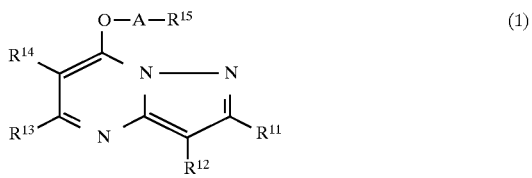

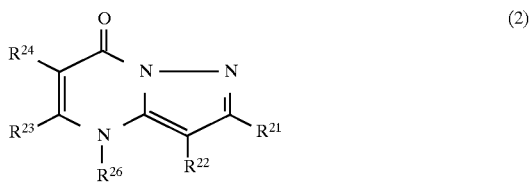

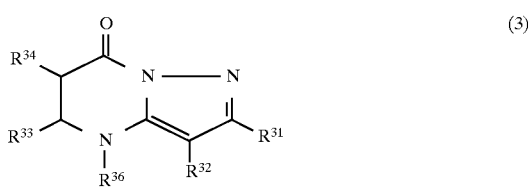

wherein the substituents are as defined herein. This composition exhibits potent analgesic activity and is effective for alleviating various types of pain such as postoperative pain.

11 Claims, No Drawings

ANALGESIC COMPOSITION OF PYRAZOLO (1,5-A) PYRIMIDINES

This application is a 371 of PCT/JP96/02759, filed Sep. 24, 1996.

TECHNICAL FIELD

The present invention relates to novel analgesic compositions comprising as an active ingredient a specific type of pyrazolo[1,5-a]pyrimidine derivative.

DISCLOSURE OF THE INVENTION

The object of this invention is to provide novel analgesic compositions which exhibit potent analgesic activity and are effective for alleviating various types of pain such as postoperative pain, migraine, gout, neurogenic pain, cancerous pain and chronic pain.

The above object can be achieved with an analgesic composition comprising as an active ingredient a specific pyrimidine derivative represented by one of the following formulas (1) to (3):

formula (1):

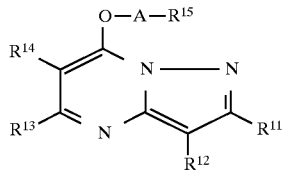

wherein $R^{11}$ represents hydrogen, lower alkyl, pyridyl, furyl, thienyl, phenyl optionally having lower alkyl or phenylthio as a substituent, N-(lower)alkylpyrrolyl or pyrazinyl; $R^{12}$ represents hydrogen, halogen, phenyl, phenyl having halogen, phenylthio or trifluoromethyl as a substituent, phenyl having trifluoromethyl and nitro as substituents, or phenyl having lower-alkoxy and phenylthio as substituents; $R^{13}$ represents hydrogen, lower alkyl optionally having oxo, ethylenedioxy, lower alkanoyloxy, lower alkoxy, lower alkylthio, carboxyl, halogen or thienyl as a substituent, lower alkenyl, cycloalkyl, or phenyl optionally having 1 to 3 substituents selected from the group consisting of lower alkyl, halogen and lower alkoxy, furyl or thienyl; $R^{14}$ represents hydrogen, carboxyl, lower alkoxycarbonyl, nitro, halogen, or lower alkyl having lower alkoxycarbonyl or the residue of an alkali metal salt of carboxylic acid as a substituent; $R^{13}$ and $R^{14}$ may conjointly form lower alkylene; $R^{15}$ represents hydrogen, alkali metal, lower alkyl, phenyl optionally having 1 to 3 substituents selected from the group consisting of lower alkyl and lower alkoxy, pyridyl optionally having lower alkyl or halogen as a substituent, quinolyl or isoquinolyl; and A represents a single bond or lower alkylene;

formula (2):

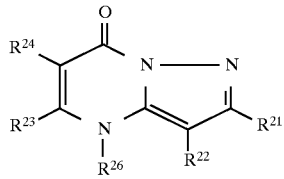

wherein $R^{21}$ represents hydrogen, phenyl, N-(lower)alkylpyrrolyl or pyridyl; $R^{22}$ represents hydrogen; $R^{23}$ represents hydrogen, lower alkyl or hydroxyl; $R^{24}$ represents hydrogen or cyano; $R^{23}$ and $R^{24}$ may conjointly form lower alkylene or $—C(NH_2)=N—N(CH_3)—$; and $R^{26}$ represents lower alkyl, lower alkoxycarbonyl, 4-phenylthiobenzyl, 2-propynyl, 2-piperidinocarbonylethyl or 5-dimethylaminocarbonylpentyl; and formula (3):

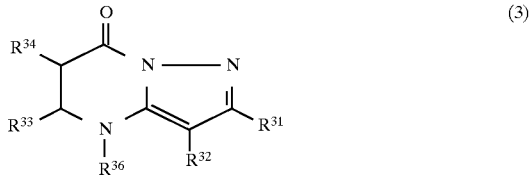

wherein $R^{31}$ represents hydrogen or N-(lower)alkylpyrrolyl; $R^{32}$ represents hydrogen; $R^{33}$ represents lower alkyl; $R^{34}$ represents cyano; $R^{33}$ and $R^{34}$ may conjointly form $=C(NH_2)—N(CH_3)—N=$; and $R^{36}$ represents hydrogen or lower alkyl.

The analgesic compositions of the invention exhibit highly potent analgesic activity and are effective for relieving various types of pain such as postoperative pain, migraine, gout, neurogenic pain and cancerous pain. These analgesic compositions produce no side effects typically seen in conventional analgesics and have no danger of causing hallucination, derangement, addiction or habituation.

Examples of each group in formulas (1) to (3) are as follows, the formulas representing the active ingredient compounds in the analgesic compositions of the invention.

The lower alkyl group includes straight- or branched-chain lower alkyl groups such as methyl, ethyl, propyl, isopropyl, butyl, isobutyl, tert-butyl, pentyl and hexyl.

The pyridyl group includes 2-pyridyl, 3-pyridyl and 4-pyridyl; the furyl group includes 2-furyl and 3-furyl; and the thienyl group includes 2-thienyl and 3-thienyl.

The phenyl group optionally having lower alkyl or phenylthio as a substituent includes phenyl, 2-methylphenyl, 3-methylphenyl, 4-methylphenyl, 2-ethylphenyl, 4-ethylphenyl, 4-butylphenyl, 4-hexylphenyl, 2-phenylthiophenyl, 3-phenylthiophenyl, 4-phenylthiophenyl and the like.

The N-(lower)alkylpyrrolyl group includes N-methyl-2-pyrrolyl, N-methyl-3-pyrrolyl, N-ethyl-2-pyrrolyl, N-butyl-3-pyrrolyl, N-hexyl-2-pyrrolyl and the like.

The pyrazinyl group includes 2-pyrazinyl and 3-pyrazinyl.

The halogen atom includes fluorine, chlorine, bromine and iodine.

The phenyl group having halogen, phenylthio or trifluoromethyl as a substituent includes 2-fluorophenyl, 3-fluorophenyl, 4-fluorophenyl, 2-bromophenyl, 3-bromophenyl, 4-bromophenyl, 2-chlorophenyl, 3-chlorophenyl, 4-chlorophenyl, 2-iodophenyl, 3-iodophenyl, 4-iodophenyl, 2-phenylthiophenyl, 3-phenylthiophenyl, 4-phenylthiophenyl, 2-trifluoromethylphenyl, 3-trifluoromethylphenyl, 4-trifluoromethylphenyl and the like.

The phenyl group having trifluoromethyl and nitro as substituents includes 4-nitro-3-trifluoromethylphenyl, 4-nitro-2-trifluoromethylphenyl, 2-nitro-4-trifluoromethylphenyl and the like.

The phenyl group having lower alkoxy and phenylthio as substituents includes 3-methoxy-4-phenylthiophenyl, 3-ethoxy-4-phenylthiophenyl, 3-propoxy-4-phenylthiophenyl, 3-butoxy-4-phenylthiophenyl, 3-pentyloxy-4-phenylthiophenyl, 3-hexyloxy-4-phenylthiophenyl, 2-methoxy-4-phenylthiophenyl, 2-butoxy-4-phenylthiophenyl, 2-hexyloxy-4-phenylthiophenyl and the like.

The lower alkyl group optionally having oxo, ethylenedioxy, lower alkanoyloxy, lower alkoxy, lower alkylthio, carboxyl, halogen or thienyl as a substituent includes not only the above-mentioned unsubstituted lower alkyl groups but also acetyl, 1-oxopropyl, 2-oxopropyl, 2-oxobutyl, 3-oxobutyl, 3-oxopentyl, 4-oxopentyl, 4-oxohexyl, 5-oxohexyl, ethylenedioxymethyl, 1,1-ethylenedioxyethyl, 2,2-ethylenedioxyethyl, 1,1-ethylenedioxypropyl, 2,2-ethylenedioxypropyl, 3,3-ethylenedioxypropyl, 1,1-ethylenedioxybutyl, 2,2-ethylenedioxybutyl, 3,3-ethylenedioxybutyl, 4,4-ethylenedioxybutyl, 3,3-ethylenedioxypentyl, 4,4-ethylenedioxyhexyl, 5,5-ethylenedioxyhexyl, acetyloxymethyl, 2-acetyloxyethyl, 3-acetyloxypropyl, 3-acetyloxybutyl, 4-acetyloxybutyl, 3-propionyloxybutyl, 3-butyryloxybutyl, 3-valeryloxypentyl, 3-hexanoyloxyhexyl, 4-acetyloxypentyl, 5-acetyloxypentyl, 4-acetyloxyhexyl, 5-acetyloxyhexyl, 6-acetyloxyhexyl, methoxymethyl, ethoxymethyl, propoxymethyl, butoxymethyl, pentyloxymethyl, hexyloxymethyl, 1-methoxyethyl, 2-methoxyethyl, 2-ethoxyethyl, 2-propoxyethyl, 2-butoxyethyl, 2-pentyloxyethyl, 2-hexyloxyethyl, 3-methoxypropyl, 3-ethoxypropyl, 2-methoxybutyl, 4-ethoxybutyl, 3-methoxypentyl, 5-ethoxypentyl, 4-methoxyhexyl, 6-ethoxyhexyl, methylthiomethyl, ethylthiomethyl, propylthiomethyl, butylthiomethyl, pentylthiomethyl, hexylthiomethyl, 1-methylthioethyl, 2-methylthioethyl, 2-ethylthioethyl, 2-methylthiopropyl, 3-methylthiopropyl, 3-ethylthiobutyl, 4-butylthiobutyl, 5-methylthiopentyl, 6-ethylthiohexyl, carboxymethyl, 1-carboxyethyl, 2-carboxyethyl, 2-carboxypropyl, 3-carboxypropyl, 4-carboxybutyl, 5-carboxypentyl, 6-carboxyhexyl, fluoromethyl, bromomethyl, chloromethyl, iodomethyl, 2-chloroethyl, 2-bromopropyl, 3-iodopropyl, 4-fluorobutyl, 5-chloropentyl, 6-bromohexyl, 2-thienylmethyl, 1-(2-thienyl)ethyl, 2-(2-thienyl)ethyl and the like.

The lower alkenyl group includes vinyl, allyl, isopropenyl, 3-butenyl, 4-pentenyl, 5-hexenyl and the like.

The cycloalkyl group includes cyclopropyl, cyclobutyl, cyclopentyl, cyclohexyl, cycloheptyl, cyclooctyl and the like.

The phenyl group optionally having 1 to 3 substituents selected from the group consisting of lower alkyl, halogen and lower alkoxy includes phenyl, 2-methylphenyl, 3-methylphenyl, 4-methylphenyl, 4-ethylphenyl, 4-propylphenyl, 4-butylphenyl, 4-t-butylphenyl, 4-pentylphenyl, 4-hexylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-fluorophenyl, 3-fluorophenyl, 4-fluorophenyl, 2-bromophenyl, 3-bromophenyl, 4-bromophenyl, 2-chlorophenyl, 3-chlorophenyl, 4-chlorophenyl, 2-iodophenyl, 3-iodophenyl, 4-iodophenyl, 2,4-dichlorophenyl, 2-bromo-4-chlorophenyl, 3,4,5-trichlorophenyl, 2,4,6-trichlorophenyl, 2-methoxyphenyl, 3-methoxyphenyl, 4-methoxyphenyl, 4-ethoxyphenyl, 4-propoxyphenyl, 4-butoxyphenyl, 4-pentyloxyphenyl, 4-hexyloxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxyphenyl, 3,4,5-trimethoxyphenyl, 3,4,5-triethoxyphenyl and the like.

The lower alkoxy group includes methoxy, ethoxy, propoxy, isopropoxy, butoxy, pentyloxy, hexyloxy, and the like.

The lower alkoxycarbonyl group includes methoxycarbonyl, ethoxycarbonyl, propoxycarbonyl, isopropoxycarbonyl, butoxycarbonyl, pentyloxycarbonyl, hexyloxycarbonyl and the like.

The alkali metal atom and alkali metal of alkali metal salt include sodium, potassium, lithium and the like.

The lower alkyl group having lower alkoxycarbonyl or the residue of an alkali metal salt of carboxylic acid as a substituent includes methoxycarbonylmethyl, ethoxycarbonylmethyl, propoxycarbonylmethyl, butoxycarbonylmethyl, pentyloxycarbonylmethyl, hexyloxycarbonylmethyl, 2-methoxycarbonylethyl, 2-ethoxycarbonylpropyl, 4-methoxycarbonylbutyl, 5-ethoxycarbonylpentyl, 5-ethoxycarbonylhexyl, sodiumoxycarbonylmethyl, potassiumoxycarbonylmethyl, lithiumoxycarbonylmethyl, 2-sodiumoxycarbonylethyl, 2-potassiumoxycarbonylethyl, 2-lithiumoxycarbonylethyl, 3-sodiumoxycarbonylpropyl, 4-lithiumoxycarbonylbutyl, 5-sodiumoxycarbonylpentyl, 6-lithiumoxycarbonylhexyl and the like.

The lower alkylene group includes methylene, ethylene, methylmethylene, trimethylene, tetramethylene, pentamethylene, hexamethylene and the like.

The phenyl group optionally having 1 to 3 substituents selected from the group consisting of lower alkyl and lower alkoxy includes phenyl, 2-methylphenyl, 3-methylphenyl, 4-methylphenyl, 4-ethylphenyl, 4-propylphenyl, 4-butylphenyl, 4-t-butylphenyl, 4-pentylphenyl, 4-hexylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methoxyphenyl, 3-methoxyphenyl, 4-methoxyphenyl, 4-ethoxyphenyl, 4-propoxyphenyl, 4-butoxyphenyl, 4-pentyloxyphenyl, 4-hexyloxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxyphenyl, 3,4,5-trimethoxyphenyl, 3,4,5-triethoxyphenyl, 3-methoxy-4-methylphenyl and the like.

The pyridyl group optionally having lower alkyl or halogen as a substituent includes not only the above-mentioned unsubstituted pyridyl but also 6-methyl-2-pyridyl, 6-ethyl-2-pyridyl, 6-propyl-2-pyridyl, 6-butyl-2-pyridyl, 6-pentyl-2-pyridyl, 6-hexyl-2-pyridyl, 6-methyl-3-pyridyl, 2-methyl-4-pyridyl, 5-methyl-2-pyridyl, 4-methyl-2-pyridyl, 6-chloro-2-pyridyl, 6-bromo-2-pyridyl, 6-fluoro-2-pyridyl, 6-iodo-2-pyridyl, 5-chloro- 2-pyridyl, 5-bromo-2-pyridyl, 5-fluoro-2-pyridyl, 5-iodo-2-pyridyl, 6-chloro-3-pyridyl, 2-chloro-4-pyridyl, 4-chloro-2-pyridyl and like substituted pyridyl groups.

The quinolyl group includes 2-quinolyl, 3-quinolyl, 4-quinolyl, 5-quinolyl, 6-quinolyl, 7-quinolyl and 8-quinolyl.

The isoquinolyl group includes 1-isoquinolyl, 3-isoquinolyl, 4-isoquinolyl, 5-isoquinolyl, 6-isoquinolyl, 7-isoquinolyl and 8-isoquinolyl.

Among the pyrazolo[1,5-a]pyrimidine derivatives of formula (1) for use as an active ingredient of the analgesic composition of the invention, the following compounds are preferred: compounds wherein $R^{11}$ represents hydrogen or lower alkyl, $R^{12}$ and $R^{14}$ represent hydrogen, $R^{13}$ represents lower alkyl, $R^{15}$ represents hydrogen, pyridyl or phenyl having 3 lower alkoxy groups as substituents, and A represents a single bond or methylene; and compounds wherein $R^{12}$ represents halogen, $R^{11}$ and $R^{14}$ represent hydrogen, $R^{13}$ represents lower alkyl or lower alkenyl, $R^{15}$ represents pyridyl and A represents methylene. Of these, those wherein $R^{12}$ represents hydrogen are particularly preferred.

The preferred active ingredient compounds include the following five groups of compounds of formula (1) having a combination of radicals defined below:

1) compounds wherein $R^{11}$ represents lower alkyl, $R^{13}$ represents n-butyl, $R^{14}$ represents hydrogen, $R^{15}$ represents pyridyl or phenyl having 3 lower alkoxy groups as substituents and A represents methylene;
2) compounds wherein $R^{11}$ represents hydrogen, $R^{13}$ and $R^{14}$ conjointly form tetramethylene, $R^{15}$ represents pyridyl and A represents methylene;
3) compounds wherein $R^{11}$ and $R^{14}$ represent hydrogen, $R^{13}$ represents cycloalkyl, (lower)alkoxy(lower)alkyl, (lower)alkylthio(lower)alkyl or phenyl, $R^{15}$ represents pyridyl and A represents methylene;
4) compounds wherein $R^{11}$ and $R^{14}$ represent hydrogen, $R^{13}$ represents n-butyl, $R^{15}$ represents hydrogen, lower alkyl, pyridyl optionally having lower alkyl or halogen as a substituent, quinolyl or isoquinolyl and A represents a single bond; and
5) compounds wherein $R^{11}$ and $R^{14}$ represent hydrogen, $R^{13}$ represents n-butyl, $R^{15}$ represents phenyl having 2 or 3 lower alkoxy groups as substituents, pyridyl or quinolyl and A represents lower alkylene.

Of these five groups of preferred active ingredient compounds of the invention, the following compounds are particularly preferred:

[1] compounds wherein $R^{11}$ represents lower alkyl, $R^{13}$ represents n-butyl, $R^{14}$ represents hydrogen, $R^{15}$ represents pyridyl and A represents methylene;
[2] compounds wherein $R^{11}$ represents hydrogen, $R^{13}$ and $R^{14}$ conjointly form tetramethylene, $R^{15}$ represents pyridyl and A represents methylene;
[3] compounds wherein $R^{11}$ and $R^{14}$ represent hydrogen, $R^{13}$ represents cyclohexyl or phenyl, $R^{15}$ represents pyridyl and A represents methylene;
[4] compounds wherein $R^{11}$ and $R^{14}$ represent hydrogen, $R^{13}$ represents n-butyl, $R^{15}$ represents hydrogen, lower alkyl, halogen-substituted pyridyl or isoquinolyl and A represents a single bond; and
[5] compounds wherein $R^{11}$ and $R^{14}$ represent hydrogen, $R^{13}$ represents n-butyl, $R^{15}$ represents phenyl having 2 or 3 lower alkoxy groups as substituents or pyridyl and A represents lower alkylene.

Of these groups of compounds, particularly preferred are those wherein $R^{11}$ and $R^{14}$ represent hydrogen, $R^{13}$ represents n-butyl, $R^{15}$ represents hydrogen or pyridyl and A represents a single bond or lower alkylene.

The most preferred active ingredient compound of the invention is 5-n-butyl-7-(4-pyridylmethoxy)pyrazolo[1,5-a]pyrimidine or 5-n-butyl-7-hydroxypyrazolo[1,5-a]pyrimidine.

Generally, the active ingredient compounds of the invention are known compounds, which can be produced, for example, using suitable starting materials as shown below. Exemplary processes for production of the compounds of formula (1) to (3) are schematically shown hereinafter.

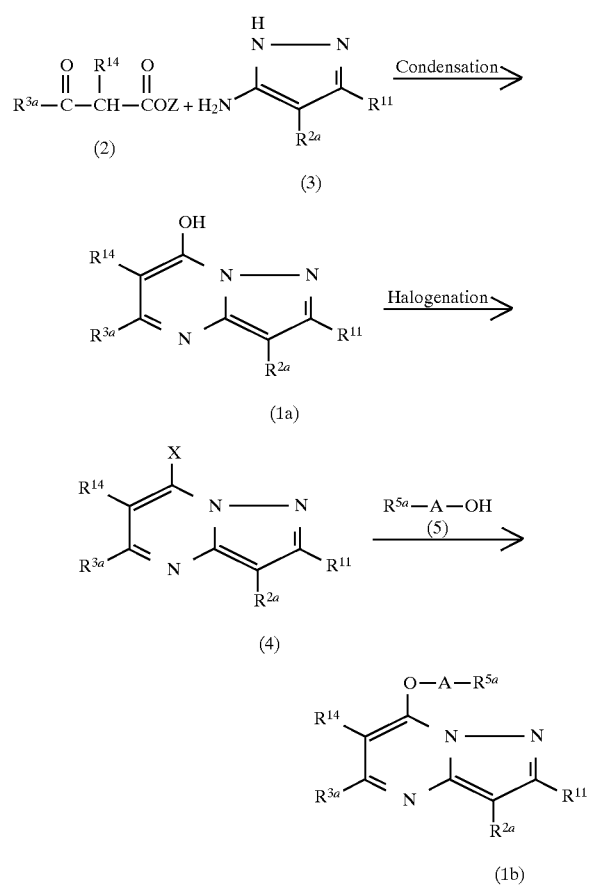

wherein $R^{11}$, and A are as defined above, $R^{2a}$ represents hydrogen, phenyl, phenyl having halogen, phenylthio or trifluoromethyl as a substituent, phenyl having trifluoromethyl and nitro as substituents, or phenyl having lower alkoxy and phenylthio as substituents, $R^{3a}$ is lower alkyl optionally having lower alkoxy, lower alkylthio, carboxyl or halogen as a substituent, lower alkenyl, cycloalkyl, phenyl optionally having 1 to 3 substituents selected from the group consisting of lower alkyl, halogen and lower alkoxy, furyl or thienyl; $R^{3a}$ and $R^{14}$ may conjointly form lower alkylene; $R^{5a}$ represents lower alkyl, phenyl optionally having 1 to 3 substituents selected from the group consisting of lower alkyl and lower alkoxy, pyridyl optionally having lower alkyl or halogen as a substituent, quinolyl or isoquinolyl; and X represents halogen and Z represents lower alkyl.

In Reaction Scheme-1, the condensation of the compound (2) and 3-aminopyrazole derivative (3) can be carried out in a suitable inert solvent at room temperature to the boiling point of the solvent. Suitable inert solvents include acetic acid, ethanol, benzene, toluene, xylene and tetrahydrofuran (THF). The compound (2) and 3-aminopyrazole derivative (3) are preferably used in an approximately equimolar proportion. The reaction goes to completion in about 2–5 hours to provide the desired compound (1a).

The subsequent halogenation of the compound (1a) is performed using a suitable halogenating agent such as phosphorus oxychloride or phosphorus oxybromide in the presence of a suitable deacidification agent such as N,N-dimethylaniline, N,N-diethylaniline or triethylamine. Since the above halogenating agents also function as solvents, there is no need to use other solvents in this reaction but an inert solvent such as benzene, toluene or xylene may be optionally used. The deacidification agent is used preferably in an amount of about 1–10 equivalents relative to the compound (1a) by weight. The reaction is carried out at approximately room temperature to 150° C. and completed in about 0.5–12 hours.

The halide (4) obtained in the above reaction is treated with an alcohol derivative (5) to produce a compound (1b). This reaction is usually carried out in a suitable solvent in the presence of a deacidification agent. Suitable deacidification agents include inorganic bases such as hydroxides of alkali metals such as sodium hydroxide and potassium hydroxide; hydrides of alkali metals such as lithium hydride, sodium hydride and potassium hydride; bicarbonates such as sodium hydrogencarbonate; and carbonates such as potassium carbonate; and tertiary amines such as triethylamine, N,N-diethylaniline, N-methylmorpholine, pyridine and 4-dimethylaminopyridine. Suitable solvents include lower alcohols such as methanol and ethanol; chain or cyclic ethers such as tetrahydrofuran (THF) and 1,4-dioxane; and inert solvents such as N,N-dimethylformamide (DMF) and dimethyl sulfoxide (DMSO). In the case of using an inorganic base as the deacidification agent, a mixed solvent of an inert solvent and water is preferably used. Aromatic hydrocarbons such as benzene, toluene and xylene may also be used as the solvent.

There is no specific limitation on the amounts of the alcohol derivative (5) and deacidification agent relative to the halide (4) in the above reaction. However, they are preferably used in an approximately equimolar to excessive molar amount respectively. The reaction can proceed under all of the following conditions; cooling, room temperature and heating. The reaction is carried out at 0° C. to reflux temperature of the solvent and completed in about 0.5–15 hours.

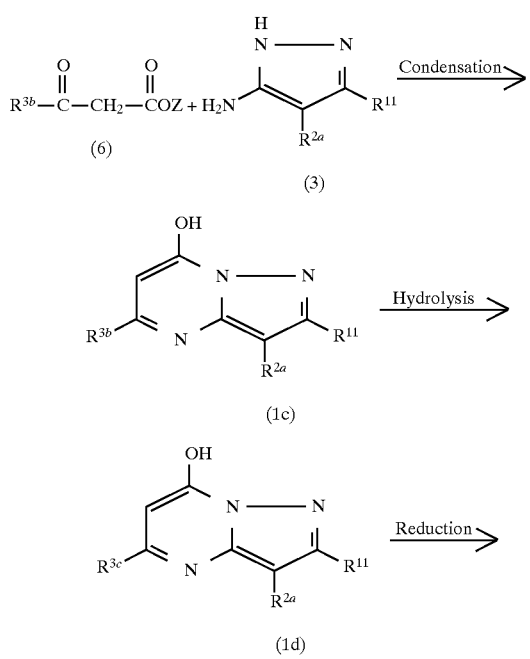

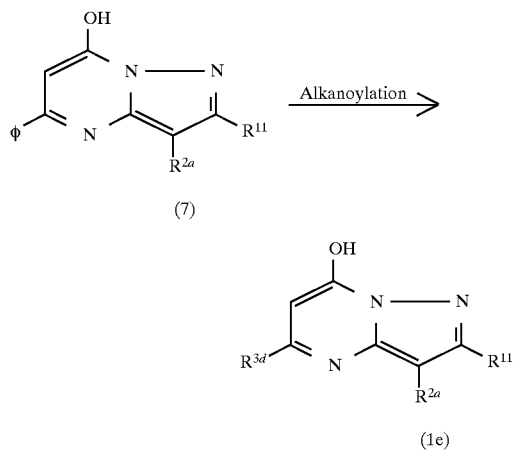

wherein $R^{11}$, $R^{2a}$, $R^{5a}$, A, X and Z are as defined above, $R^{3b}$ represents lower alkyl having protected carbonyl, $R^{3c}$ represents lower alkyl having carbonyl, φ represents hydroxy (lower)alkyl and $R^{3d}$ represents (lower)alkanoyloxy(lower) alkyl.

In Reaction Scheme-2, the condensation of the compound (6) and 3-aminopyrazole derivative (3) can be carried out in the same manner as the condensation of the compound (2) and aminopyrazole derivative (3) in Reaction Scheme-1.

Referring to "lower alkyl having protected carbonyl" represented by $R^{3b}$ in the compound (6), specific examples are lower alkyl groups having as protected carbonyl the residue of di(lower)alkylacetal such as dimethylacetal, methylethylacetal, diethylacetal, dipropylacetal, dibutylacetal, dipentylacetal or dihexylacetal and lower alkyl groups having as protected carbonyl the residue of cyclic acetal such as ethyleneacetal, trimethyleneacetal or tetramethyleneacetal.

The subsequent hydrolysis of the compound (1c) according to Reaction Scheme-2 can be carried out using an organic acid such as acetic acid, propionic acid or p-toluenesulfonic acid. Of these organic acids, carboxylic acids such as acetic acid and propionic acid function as solvents. When such a carboxylic acid is used, no other solvents are necessary. Even in this case, other suitable inert solvents such as benzene, toluene and xylene may be optionally used. The reaction is carried out at approximately room temperature to reflux temperature of the solvent and completed in about 10–80 hours to provide the compound (1d).

Referring to "lower alkyl having carbonyl" represented by $R^{3C}$ in the compound (1d), examples are those obtained by elimination of the protective group from the corresponding "lower alkyl having protected carbonyl" represented by $R^{3b}$. Specific examples are formyl, formylmethyl, acetyl, 2-formylethyl, 2-oxopropyl, propionyl, 3-formylpropyl, 3-oxobutyl, 2-oxobutyl, butyryl, 4-formylbutyl, 4-oxopentyl, 3-oxopentyl, 2-oxopentyl, valeryl, 5-formylpentyl, 5-oxohexyl, 4-oxohexyl, 3-oxohexyl, 2-oxohexyl, hexanoyl and the like.

The subsequent reduction of the compound (1d) is carried out using a suitable reducing agent in an inert solvent. Suitable reducing agents include boron hydride compounds such as sodium borohydride, potassium borohydride, lithium borohydride, sodium cyanoborohydride and sodium triethylborohydride; and lithium aluminium hydride compounds such as lithium aluminium hydride and lithium tributoxyaluminohydride. When a boron hydride compound is used as the reducing agent, suitable inert solvents are alcohol solvents such as methanol and ethanol or mixed solvents of said alcohol and another solvent such as dichloromethane or diethyl ether. When a lithium aluminium hydride compound is used as the reducing agent, suitable solvents are diethyl ether, THF and like ethers. The reducing agent is preferably used in at least approximately equimolar proportion relative to the compound (1d). The reaction is carried out at approximately 0° C. to room temperature and completed in about 0.5–3 hours.

The compound (7) thus obtained is alkanoylated using an alkanoylating agent in the absence of solvents or in an inert solvent such as pyridine, lutidine, DMF or DMA. Suitable alkanoylating agents include acid anhydrides such as acetic anhydride, propionic anhydride, butyric anhydride, valeric anhydride, hexanoic anhydride and heptanoic anhydride. These are generally used in an amount of 1–10 equivalents relative to the compound (7). In order not to alkanoylate the hydroxyl group at 7-position of the compound (7), the reaction conditions are preferably selected from a temperature range of approximately 0° C. to room temperature and a reaction time range of about 0.5 to 2 hours.

[Reaction Scheme-3]

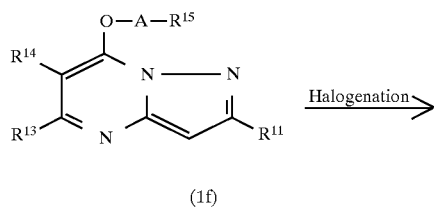

(1f)

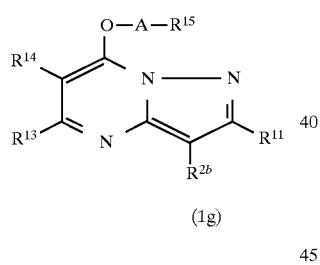

(1g)

wherein $R^{11}$, $R^{13}$, $R^{14}$, $R^{15}$ and A are as defined above and $R^{2b}$ represents halogen.

The halogenation of the compound (1f) in Reaction Scheme-3 can be carried out using a halogenating agent such as N-bromosuccinimide (NBS), N-chlorosuccinimide (NCS) or bromine in an inert solvent such as dimethoxyethane, dimethoxyethane-water, benzene or carbon tetrachloride. The halogenating agent is normally used in an amount of 1 equivalent to a slightly excessive amount relative to the compound (1f). The reaction is carried out at approximately 0° C. to room temperature and completed in about 0.5–5 hours.

[Reaction Scheme-4]

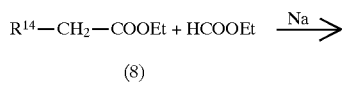

(8)

-continued
[Reaction Scheme-4]

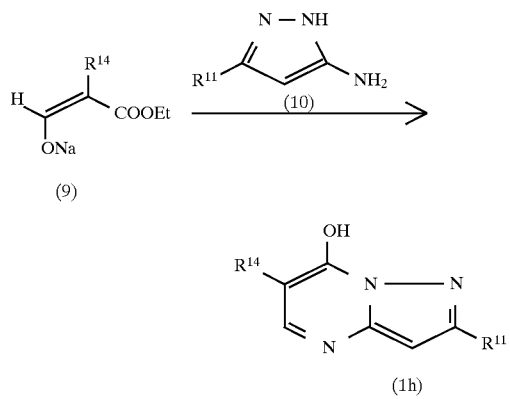

wherein $R^{11}$ and $R^{14}$ are as defined above.

As shown in Reaction Scheme-4, the compound (8) and ethyl formate are reacted to produce a compound (9). This reaction can be carried out in an inert solvent such as methanol, ethanol, t-butanol, benzene, xylene, toluene, dichloromethane, chloroform, acetic acid or methanol-water in the presence of Na in an equimolar to slightly excessive amount relative to the compound (8). Ethyl formate is used in an equimolar to slightly excessive amount relative to the compound (8). The reaction is usually carried out at approximately room temperature and completed in about 0.5–20 hours.

Subsequently an ethanol solution of aminopyrazole (10) is added to the reaction system and allowed to react to form the desired compound (1h). The aminopyrazole (10) is normally used in an equimolar to slightly excessive amount relative to the compound (9). The reaction is carried out at reflux temperature of the solvent and completed in about 5 hours.

[Reaction Scheme-5]

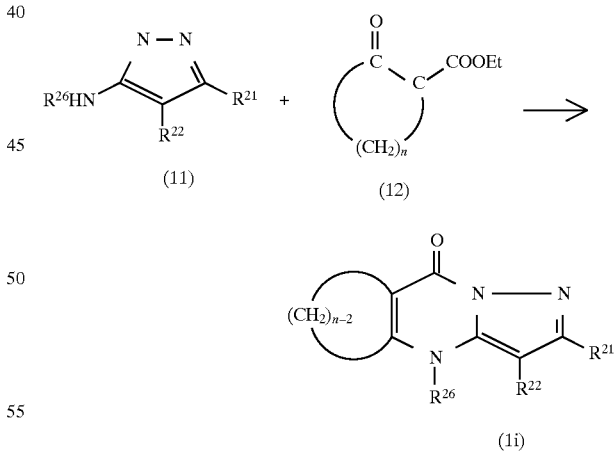

wherein $R^{21}$, $R^{22}$ and $R^{26}$ are as defined above, and n is an integer of 3–6.

The reaction between the compounds (11) and (12) in Reaction Scheme-5 can be carried out in an inert solvent such as acetic acid or toluene using the compound (12) in an equimolar to slightly excessive amount relative to the compound (11). The reaction is carried out at about 100° C. and completed in 3 to 10 hours to provide the desired compound (1i).

[Reaction Scheme-6]

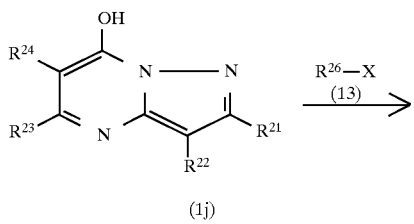

(1j)

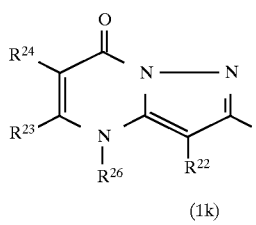

(1k)

wherein $R^{21}$, $R^{22}$, $R^{23}$, $R^{24}$, $R^{26}$ and X are as defined above.

The reaction between the compounds (1j) and (13) in Reaction Scheme-6 can be carried out in DMF in the presence of $K_2CO_3$ in an amount of equimolar to slightly excessive amount relative to the compound (1j). The compound (13) is used in an equimolar to slightly excessive amount relative to the compound (1j). The reaction is carried out at about 60° C. and completed in about 4 to 10 hours to provide the desired compound (1k).

wherein $R^{21}$, $R^{22}$, and $R^{26}$ are as defined above.

According to Reaction Scheme-7, the compounds (14) and (15) are reacted to form a compound (16). The compound (16) is reacted with the compound (17) to form a compound (18) which is then reacted with MCPBA to produce a compound (19). The compound (19) is reacted with $MeNHNH_2$ to produce the desired compounds (11) and (1m).

These reactions can be carried out under the following conditions. The reaction between the compounds (14) and (15) can be carried out using $K_2CO_3$ in an equimolar to slightly excessive amount relative to the compound (14) at about 150° C. for about 3 hours.

The reaction between the compounds (16) and (17) can be carried out in the same manner as the reaction between the compounds (1j) and (13) in Reaction Scheme-6.

The reaction between the compound (18) and MCPBA can be carried out using MCPBA in an approximately equimolar proportion relative to the compound (18) in an suitable solvent such as methylene chloride or chloroform at about 0° C. for about 3 hours.

The reaction between the compound (19) and $MeNHNH_2$ can be carried out, for example, in ethanol using about 1 equivalent of triethylamine and about 2.5 equivalents of $MeNHNH_2$ relative to the compound (19). When this reaction is carried out at 60° C. for about 30 minutes, the compound (11) is selectively obtained. When the same reaction is carried out at 100° C. for about 20 minutes, the compound (1m) is mainly obtained.

[Reaction Scheme-7]

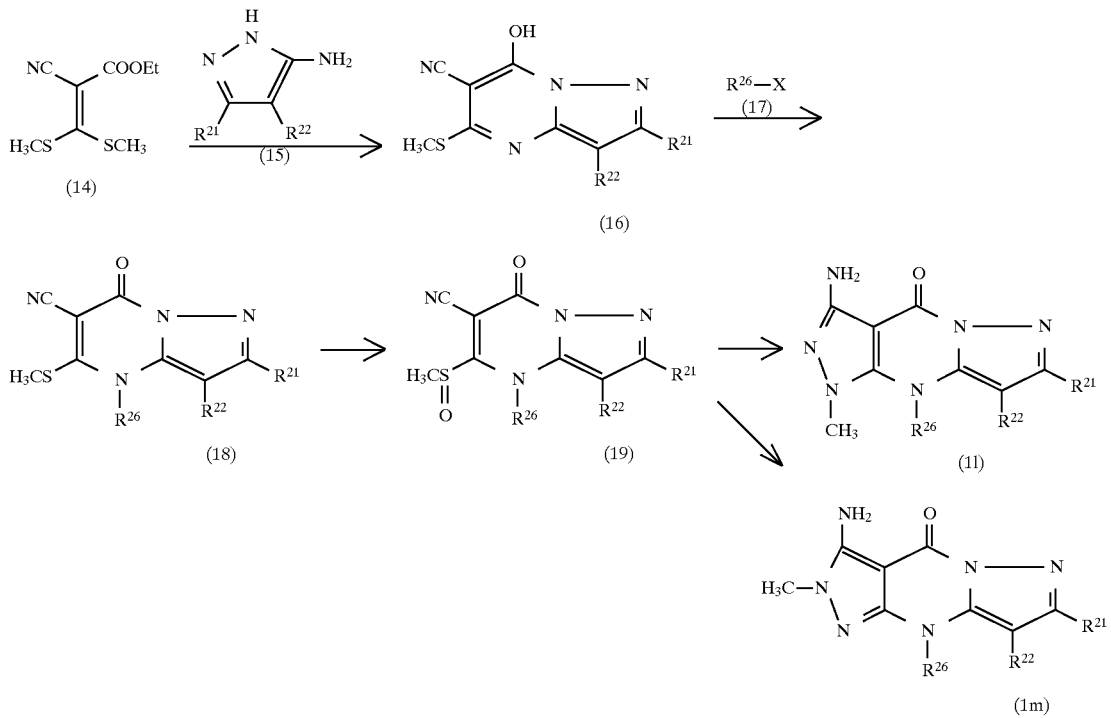

[Reaction Scheme-8]

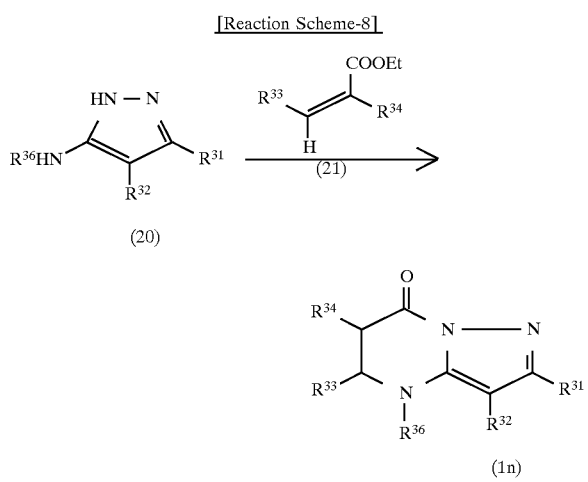

wherein $R^{31}$, $R^{32}$, $R^{33}$, $R^{34}$ and $R^{36}$ defined above.

The reaction between the compounds (20) and (21) in Reaction Scheme-8 can be carried out in an inert solvent such as ethanol at approximately room temperature using the compound (21) in an equimolar to slightly excessive amount relative to the compound (20). The reaction goes to completion in about 48 hours to provide the desired compound (1n).

Some active ingredient compounds of the invention can be formed into pharmaceutically acceptable acid addition salts. Such salts are included among the active ingredient compounds of the invention. Suitable acids for use to form such acceptable acid addition salts are inorganic acids such as hydrochloric acid, hydrobromic acid and sulfuric acid; and organic acids such as oxalic acid, fumaric acid, maleic acid, tartaric acid and citric acid. These acid addition salts can be formed according to conventional methods.

The compounds obtained according to the above-mentioned processes can be easily isolated by conventional separation and purification methods. Useful isolation methods include various conventional methods such as adsorption chromatography, preparative thin-layer chromatography, recrystallization and solvent extraction.

Some active ingredient compounds of the invention represented by formulas (1) to (3) may exist as optical isomers having an carbon atom as an asymmetric center. Such optical isomers (racemic derivatives, R-derivatives, and S-derivatives) are included among the active ingredient compounds of the invention. Also, some active ingredient compounds of the invention may exist as cis- or trans-isomers. Any of these isomers can, of course, be used as an active ingredient of analgesic compositions of the invention.

The analgesic compositions of the invention can be shaped into general dosage forms for pharmaceutical compositions with suitable pharmaceutically acceptable carrier(s). Examples of useful pharmaceutically acceptable carriers include conventional diluents or excipients such as fillers, volume builders, binders, humectants, disintegrators, surfactants, lubricants, and the like. These carriers are selectively used according to the desired unit dosage form.

The unit dosage form for analgesic compositions of the invention can be selected from a broad variety of forms according to the intended medical treatment. Typical examples are tablets, pills, powders, solutions, suspensions, emulsions, granules, capsules, suppositories, injections (solutions, suspensions, etc.), ointments, and the like.

The tablets can be molded using as pharmaceutically acceptable carriers excipients such as lactose, sucrose, sodium chloride, glucose, urea, starch, calcium carbonate, kaolin, crystalline cellulose, silicic acid and potassium phosphate; binders such as water, ethanol, propanol, simple syrup, glucose syrup, starch solution, gelatin solution, carboxymethyl cellulose, hydroxypropyl cellulose, methyl cellulose and polyvinyl pyrrolidone; disintegrators such as sodium carboxymethyl cellulose, calcium carboxymethyl cellulose, low-substituted hydroxypropyl cellulose, dry starch, sodium alginate, agar powder, laminaran powder, sodium hydrogen-carbonate and calcium carbonate; surfactants such as polyoxyethylene sorbitan fatty acid esters, sodium lauryl sulfate and stearyl monoglyceride; disintegration inhibitors such as sucrose, stearin, cacao butter and hydrogenated oil; absorption promoters such as quaternary ammonium base and sodium lauryl sulfate; humectants such as glycerin and starch; adsorbents such as starch, lactose, kaolin, bentonite and colloidal silicic acid; and lubricants such as purified talc, stearic acid salt, boric acid powder and polyethylene glycol.

Furthermore, such tablets may be optionally coated to provide sugar-coated tablets, gelatin-coated tablets, enteric tablets, film-coated tablets, etc. or be processed into double-layer or multiple-layer tablets.

The pills can be molded using as pharmaceutically acceptable carriers excipients such as glucose, lactose, starch, cacao butter, hydrogenated vegetable oil, kaolin and talc; binders such as gum arabic powder, tragacanth powder, gelatin and ethanol; and disintegrators such as laminaran and agar.

The suppositories can be molded using as pharmaceutically acceptable carriers polyethylene glycol, cacao butter, higher alcohols or their esters, gelatin, semisynthetic glycerides, and the like. The capsules are usually manufactured by mixing an active ingredient compound of the invention with pharmaceutically acceptable carriers as mentioned above and filling the mixture into hard gelatin capsule shells, soft capsule shells, etc. according to conventional methods.

The injections in the form of solutions, emulsions, suspensions, etc. can be manufactured using diluents such as water, ethyl alcohol, macrogol, propylene glycol, ethoxylated isostearyl alcohol, polyoxylated isostearyl alcohol and polyoxyethylene sorbitan fatty acid esters and are preferably sterilized and rendered isotonic with respect to the blood. Sodium chloride, glucose or glycerin in an amount sufficient for providing an isotonic solution may be incorporated into the pharmaceutical composition of the invention. Conventional solubilizers, buffers, soothing agents, etc. may also be added.

Further, coloring agents, preservatives, perfumes, flavors, sweeteners, or other medicines may be optionally incorporated in the pharmaceutical compositions of the invention.

The ointments in the form of paste, cream, gel, etc. can be manufactured using diluents such as white vaseline, paraffin, glycerin, cellulose derivatives, polyethylene glycol, silicone and bentonite.

The proportion of the active ingredient compound of formulas (1) to (3) in the pharmaceutical composition of the invention is not so critical but can be liberally selected from a broad range. Generally, the active ingredient compound preferably accounts for about 1 to 70 weight % of the final composition.

There is no specific limitation on methods for administering the pharmaceutical compositions of the invention. The proper method can be determined according to the dosage form, patient's age, sex or other conditions, severity of disease, etc. For example, the tablets, pills, solutions, suspensions, emulsions, granules and capsules are orally administered. The injections are intravenously administered singly or in admixture with a conventional replenisher such as glucose or amino acid, and optionally administered singly by the intramuscular, intradermal, subcutaneous or intraperitoneal route. The suppositories are intrarectally administered.

The dosage of the pharmaceutical composition is suitably selected according to the administration method, patient's age, sex or other conditions, severity of disease, etc. The dosage of the active ingredient compound of the invention is preferably about 0.5–20 mg, more preferably about 1–10 mg, per kg body weight a day and this amount can be administered once or in 2–4 divided doses a day.

BEST MODE FOR CARRYING OUT THE INVENTION

The present invention is described below in more detail with reference to Production Examples and Reference Examples. Production Examples illustrate preparation examples for active ingredient compounds of the invention, and Reference Examples those for the starting compounds for preparing the active ingredient compounds of the invention.

Production Example 1

Preparation of 5-n-butyl-7-hydroxypyrazolo[1,5-a] pyrimidine

A suspension of 100 g of 3-aminopyrazole and 190 g of methyl 3-oxoheptanoate in 120 ml of toluene was heated under reflux at 100° C. for 3 hours and cooled. Toluene was distilled off under reduced pressure, and diethyl ether was added to the residue. The crystals precipitated were collected and sequentially washed with diethyl ether and acetonitrile to provide 184 g of 5-n-butyl-7-hydroxypyrazolo[1,5-a] pyrimidine as colorless crystals. The structure and melting point of the compound obtained are shown in Table 1 below.

Production Examples 2–42

Compounds Nos. 2–42 set forth in Table 1 were prepared in the same manner as in Production Example 1. The structures and melting points or NMR data for the compounds obtained are also shown in Table 1.

Reference Example 1

Preparation of 5-n-butyl-7-chloropyrazolo[1,5-a] pyrimidine

Phosphorus oxychloride (80 ml) and triethylamine (44 ml) were added to a suspension of 40 g of the crystals obtained in Production Example 1 in 400 ml of toluene. The mixture was heated under reflux for 4 hours. After completion of the reaction, the reaction mixture was concentrated under reduced pressure and the residue was poured into ice water. The mixture was neutralized with sodium acetate and extracted with ethyl acetate. The organic layer was collected, washed with a saturated saline solution, dried over anhydrous sodium sulfate and concentrated under reduced pressure. The residue was purified by silica gel column chromatography (eluent: ethyl acetate:n-hexane=1:9) to provide 41 g of the title compound as a light yellow oily compound.

$^1$H-NMR($\delta$: ppm) [CDCl$_3$] 0.96 (3H, t, J=7.3), 1.4–1.5 (2H, m), 1.7–1.8 (2H, m), 2.83 (2H, t, J=7.8), 6.69 (1H, d, J=2.3), 6.86 (1H, s), 8.17 (1H, d, J=2.3)

The following compounds were produced in the same manner as above.

(1) 7-Chloro-5-methylpyrazolo[1,5-a]pyrimidine
oily compound
$^1$H-NMR($\delta$: ppm) [CDCl$_3$] 2.61 (3H, s), 6.67 (1H, d, J=2.5), 6.86 (1H, s), 8.17 (1H, d, J=2.5)
(2) 5-n-Butyl-7-chloro-2-methylpyrazolo[1,5-a]pyrimidine
oily compound
$^1$H-NMR($\delta$: ppm) [CDCl$_3$] 0.96 (3H, t, J=7.4), 1.3–1.5 (2H, m), 1.7–1.8 (2H, m), 2.55 (3H, s), 2.79 (2H, t, J=7.7), 6.46 (1H, s), 6.76 (1H, s)
(3) 7-Chloro-5-phenylpyrazolo[1,5-a]pyrimidine
crystals
$^1$H-NMR($\delta$: ppm) [CDCl$_3$] 6.81 (1H, d, J=2.3), 7.40 (1H, s), 7.4–7.6 (3H, m), 8.0–8.1 (2H, m), 8.21 (1H, d, J=2.3)
(4) 7-Chloro-5-cyclopentylpyrazolo[1,5-a]pyrimidine oily compound
$^1$H-NMR($\delta$: ppm) [CDCl$_3$] 1.6–1.9 (6H, m), 2.0–2.2 (2H, m), 3.1–3.3 (1H, m), 6.68 (1H, d, J=2.0), 6.87 (1H, s), 8.16 (1H, d, J=2.0)
(5) 7-Chloro-5-cyclohexylpyrazolo[1,5-a]pyrimidine oily compound
$^1$H-NMR($\delta$: ppm) [CDCl$_3$] 1.2–1.6 (5H, m), 1.7–2.1 (5H, m), 2.7–2.8 (1H, m), 6.69 (1H, d, J=2.5), 6.88 (1H, s), 8.16 (1H, d, J=2.5)
(6) 7-Chloro-5-(3,5-dimethylphenyl)pyrazolo[1,5-a] pyrimidine crystals
$^1$H-NMR($\delta$: ppm) [CDCl$_3$] 2.41 (6H, s), 6.81 (1H, d, J=2.5), 7.14 (1H, s), 7.40 (1H, s), 7.67 (2H, s), 8.20 (1H, d, J=2.5)
(7) 7-Chloro-5-(3,5-dimethoxylphenyl)pyrazolo[1,5-a] pyrimidine
crystals
$^1$H-NMR($\delta$: ppm) [CDCl$_3$] 3.89 (6H, s), 6.60 (1H, t, J=2.5), 6.82 (1H, d, J=2.5), 7.21 (2H, d, J=2.5), 7.39 (1H, s), 8.22 (1H, d, J=2.5)
(8) 7-Chloro-5-(3,4,5-trimethoxyphenyl)pyrazolo[1,5-a] pyrimidine crystals
$^1$H-NMR($\delta$: ppm) [CDCl$_3$] 3.94 (3H, s), 4.00 (6H, s), 6.81 (1H, d, J=2.5), 7.31 (2H, s), 7.38 (1H, s), 8.22 (1H, d, J=2.5)
(9) 7-Chloro-5,6,7,8-tetrahydropyrazolo[5,1-b]quinazoline
crystals
$^1$H-NMR($\delta$: ppm) [CDCl$_3$] 1.8–2.0 (4H, m), 2.8–3.0 (4H, m), 6.61 (1H, d, J=2.3), 8.10 (1H, d, J=2.3)

Reference Example 2

Preparation of 7-chloro-5-(3-acetoxybutyl)pyrazolo [1,5-a]pyrimidine

Step (1)

The same procedure as in Production Example 1 was followed using 0.9 g of 3-aminopyrazole and 1.9 g of methyl 2-methyl-β-oxo-1,3-dioxolane-2-valerate. As a result, 1.85 g of 7-hydroxy-5-[2-(2-methyl-1,3-dioxolane- 2-yl)ethyl]pyrazolo[1,5-a]pyrimidine was obtained as colorless crystals.

Step (2)

The compound obtained in step (1) (22 g) was dissolved in 500 ml of acetic acid-water (4:1) and stirred at 50° C. for 3 days. After completion of the reaction, the reaction mixture was concentrated under reduced pressure and the remaining acetic acid-water was azeotropically distilled off with benzene. The residue was recrystallized from ethanol-n-hexane to provide 11 g of 7-hydroxy-5-(3-oxobutyl)pyrazolo[1,5-a]pyrimidine as colorless crystals.

Step (3)

The compound obtained in step (2) (5.7 g) was dissolved in 120 ml of methanol. Sodium borohydride (0.53 g) was added thereto while being ice-cooled. The mixture was stirred at 0° C. for 2 hours. After completion of the reaction, the reaction mixture was acidified by adding diluted hydrochloric acid dropwise and then extracted with chloroform. The organic layer was collected, washed with a saturated sodium chloride solution, dried over anhydrous sodium sulfate and concentrated under reduced pressure. The residue was recrystallized from ethanol-n-hexane to provide 4.16 g of 7-hydroxy-5-(3-hydroxybutyl)pyrazolo[1,5-a]pyrimidine as colorless crystals.

Step (4)

The crystals obtained in step (3) (4.16 g) were dissolved in 40 ml of acetic anhydride and 40 ml of pyridine and stirred at room temperature for 30 minutes. After completion of the reaction, the reaction mixture was concentrated under reduced pressure and the residue was recrystallized from methanol-diethyl ether to provide 4.2 g of 5-(3-acetoxybutyl)-7-hydroxypyrazolo[1,5-a]pyrimidine as colorless crystals.

Step (5)

The compound obtained in step (4) was treated in the same manner as Reference Example 1. The title compound was obtained as a light yellow oily compound.

$^1$H-NMR($\delta$: ppm) [CDCl$_3$] 1.30 (3H, t, J=6.4), 2.03 (3H, s), 2.0–2.1 (2H, m), 2.8–2.9 (2H, m), 5.0–5.1 (1H, m), 6.70 (1H, d, J=2.0), 6.87 (1H, s), 8.18 (1H, d, J=2.0)

Production Example 43

Preparation of 5-methyl-7-methoxypyrazolo[1,5-a]pyrimidine

Methanol (5 ml) was added to a suspension of 0.40 g of 60% sodium hydride in 10 ml of DMF. Then a solution of 1 g of 5-methyl-7-chloropyrazolo[1,5-a]pyrimidine in 5 ml of DMF was added dropwise thereinto at 0° C. and stirred at room temperature for 2 hours. The reaction mixture was poured into ice water and the crystals precipitated were collected by filtration and recrystallized from diethyl ether to provide 0.40 g of the title compound as colorless crystals. The structure and melting point of the compound obtained are shown in Table 1.

Production Example 44–76

Compounds Nos. 44–76 set forth in Table 1 were prepared in the same manner as in Production Example 43. The structures and melting points of the compounds are also shown in Table 1.

Production Example 77

Preparation of 3-bromo-5-n-butyl-7-(4-pyridylmethoxy)pyrazolo[1,5-a]pyrimidine

NBS (0.38 g) was added to a solution of 0.5 g of 5-n-butyl-7-(4-pyridylmethoxy)pyrazolo[1,5-a]pyrimidine in 10 ml of DME-water (3:1) at 0° C. and stirred for 1 hour. The mixture was stirred at room temperature for another 2 hours to allow the reaction to proceed. Some water was added to the reaction mixture, and the crystals precipitated were collected by filtration to provide 0.6 g of the title compound as colorless crystals. The structure and melting point of the compound obtained are shown in Table 1.

Production Example 78

Preparation of 5-methyl-2-phenyl-7-sodiumoxy-6-sodiumoxycarbonylmethylpyrazolo[1,5-a]pyrimidine A solution of 1.3 g of sodium hydroxide in 25 ml of water was added to a solution of 3.2 g of 6-ethoxycarbonylmethyl-7-hydroxy-5-methyl-2-phenylpyrazolo[1,5-a]pyrimidine in 60 ml of ethanol and stirred at room temperature for 3 hours. The solvent was distilled off and the remaining water was azeotropically distilled off with ethanol. The crystals precipitated were washed with hot ethanol and collected by filtration to provide 2.7 g of the title compound as ash-colored crystals. The structure and melting point of the compound obtained are shown in Table 1.

Production Example 79

Preparation of 9-hydroxy-3-(4-phenylthio)phenyl-5,6,7,8-tetrahydropyrazolo[5,1-b]quinazoline A solution of 1.5 g of 3-amino-4-(4-phenylthio) phenylpyrazole and 1.1 g of ethyl 2-cyclohexanecarboxylate in 20 ml of acetic acid was stirred at 100° C. for 3 hours. The reaction mixture was allowed to cool at room temperature and the solvent was distilled off. The crude crystals were recrystallized from chloroform-methanol-diethyl ether to provide 1.8 g of the title compound as slight yellow crystals. The structure and melting point of the compound obtained are shown in Table 1.

Production Example 80

Compound No. 80 set forth in Table 1 was prepared in the same manner as in Production Example 79. The structure and physical property of the compound are shown in Table 1.

Production Example 81

Preparation of 4-(4-phenylthio)benzyl-7-oxo-4,7-dihydropyrazolo[1,5-a]pyrimidine Potassium carbonate (1.5 g) and 4-phenylthiobenzyl chloride (2.8 g) were added to a solution of 1.3 g of 7-hydroxypyrazolo[1,5-a]pyrimidine in 30 ml of DMF and stirred at 60° C. for 4 hours. The reaction mixture was diluted with ethyl acetate and washed with water and a saturated sodium chloride solution. The solvent was distilled off and the crude crystals obtained were recrystallized from ethyl acetate to provide 1.4 g of the title compound as colorless crystals. The structure and melting point of the compound obtained are shown in Table 1.

Production Examples 82–86

Compounds No. 82–86 set forth in Table 1 were prepared in the same manner as in Production Example 81. The structures and physical properties of the compounds are shown in Table 1.

Production Example 87

Preparation of 4H-3-amino-1,9-dihydro-9-ethyl-1-methyl-dipyrazolo[1,5-a:3',4'-d]pyrimidin-4-one Triethylamine (1.44 g) and methylhydrazine (1.44 g) were added to a solution of 3.2 g of 4-ethyl-5-methanesulfinyl-7-oxo-4,7-dihydropyrazolo[1,5-a]pyrimidine-6-carbonitrile in 100 ml of ethanol and stirred at 60° C. for 30 minutes. The reaction mixture was cooled and the crystals precipitated were collected by filtration and sequentially washed with ethanol, methanol and diethyl ether to provide 1.9 g of the title compound as colorless crystals. The structure and melting point of the compound obtained are shown in Table 1.

Production Example 88

Preparation of 6-cyano-2-(N-methylpyrrolyl)-7-oxo-5-(n-propyl)-4,5,6,7-tetrahydropyrazolo[1,5-a]pyrimidine A solution of 8 g of 2-(N-methylpyrrolyl)aminopyrazole and 8.5 g of ethyl-2-cyano-2-hexenoate in 50 ml of ethanol was stirred at room temperature for 2 days. The reaction mixture was concentrated. The residue was purified by silica gel column chromatography (developing solvent: chloroform: methanol=50:1 to 30:1) and recrystallized from diethyl ether-n-hexane to provide 5.6 g of the title compound as colorless crystals. The structure and melting point of the compound obtained are shown in Table 1.

Production Example 89

Preparation of 4H-3-amino-2,9-dihydro-9-ethyl-2-methyl-dipyrazolo[1,5-a:3',4'-d]pyrimidin-4-one Triethylamine (1.44 g) and methylhydrazine (1.44 g) were added to a solution of 3.25 g of 4-ethyl-5-methanesulfinyl-7-oxo-4,7-dihydropyrazolo[1,5-a]pyrimidine-6-carbonitrile in 60 ml of ethanol. The mixture was stirred at room temperature for 10 minutes and then stirred at 100° C. for 20 minutes. The reaction mixture was ice-cooled and the crystals precipitated were collected by filtration and sequentially washed with ethanol, methanol and diethyl ether to provide 1.2 g of the title compound as colorless crystals. The structure and melting point of the compound obtained are shown in Table 1.

TABLE 1

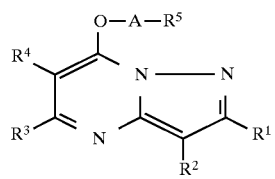

Me = Methyl, Et = Ethyl, n-Bu = n-Butyl, Ph = Phenyl, Ac = Acetyl

| No. | $R^1$ | $R^2$ | $R^3$ | $R^4$ | $R^5$ | A | Melting point (°C.) (Recrystallization solvent) |
|---|---|---|---|---|---|---|---|
| 1 | H | H | n-Bu | H | H | Single bond | 172–174 |
| 2 | 2-pyridyl | 4-F-phenyl | H | COOH | H | Single bond | ≧300 |
| 3 | 2-furyl | H | Me | H | H | Single bond | ≧280 |
| 4 | 2-thienyl | H | Me | H | H | Single bond | ≧280 (Chloroform-methanol-hexane) |
| 5 | Ph | H | Me | —CH$_2$—COOEt | H | Single bond | 241–243 |
| 6 | N-methylpyrrolyl | H | Me | H | H | Single bond | ≧280 |
| 7 | H | 4-(PhS)-phenyl | cyclopropyl | H | H | Single bond | 238–241 (Chloroform-diethyl ether) |

TABLE 1-continued

| No. | R1 | R2 | R3 | R4 | R5 | Bond | mp/Notes |
|---|---|---|---|---|---|---|---|
| 8 | 3-methylpyrazinyl | H | Me | H | H | Single bond | ≧280 (Dichloromethane-methanol-hexane) |
| 9 | H | H | CH₂=CH-CH₂-CH₂- | H | H | Single bond | 192–194 |
| 10 | H | H | cyclohexyl-CH₂- | H | H | Single bond | 259–261 |
| 11 | H | H | CH₃-C(propyl)(1,3-dioxolane) | H | H | Single bond | NMR(1) |
| 12 | H | H | CH₃-CO-CH₂-CH₂-CH₂- | H | H | Single bond | 172–174 |
| 13 | H | H | CH₃-CH(OAc)-CH₂-CH₂-CH₂- | H | H | Single bond | 151–153 (Methanol-diethyl ether) |
| 14 | H | H | CH₃-CH₂-O-CH₂-CH₂- | H | H | Single bond | NMR(2) |
| 15 | H | H | CH₃-O-CH₂-CH₂-CH₂- | H | H | Single bond | 155–157 |
| 16 | H | H | CH₃-S-CH₂-CH₂-CH₂- | H | H | Single bond | 154–156 (Chloroform-diethyl ether) |
| 17 | H | H | CH₃-CH₂-S-CH₂-CH₂- | H | H | Single bond | 164–166 (Methanol-diethyl ether) |
| 18 | H | H | HOOC-CH₂-CH₂-CH₂-CH₂- | H | H | Single bond | 231–232 |
| 19 | H | H | 4-methylphenyl | H | H | Single bond | ≧280 (Methanol) |
| 20 | H | H | 3-methylphenyl | H | H | Single bond | 235–237 (Chloroform-methanol-diethyl ether) |
| 21 | H | Ph | H | —COOEt | H | Single bond | ≧275(Decomp.) |
| 22 | H | Ph | Me | H | H | Single bond | ≧260(Decomp.) (Ethanol) |
| 23 | 4-methylphenyl | Ph | Me | H | H | Single bond | ≧280 |
| 24 | Ph | H | Me | EtOOC-CH₂-CH₂- | H | Single bond | 254–256 |

TABLE 1-continued

| # | R1 | R2 | R3 | R4 | R5 | Bond | mp (°C) |
|---|---|---|---|---|---|---|---|
| 25 | Ph | H | 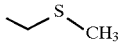 S-CH3 (ethylthio-methyl) | H | H | Single bond | 248–250 |
| 26 | H | 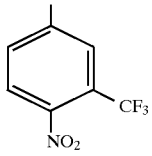 (4-CF3, 3-NO2 phenyl) | H | NO2 | H | Single bond | 281–283 |
| 27 | H | 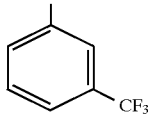 (3-CF3-phenyl) | H | H | H | Single bond | ≥280 (Chloroform-methanol-diethyl ether) |
| 28 | H | H | H | H | H | Single bond | ≥280 |
| 29 | Ph | H |  CH2Cl | H | H | Single bond | ≥300 |
| 30 | Ph | H | Me | Cl | H | Single bond | ≥300 |
| 31 |  (2-pyridyl) | 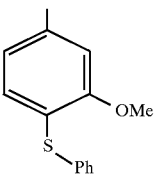 (2-OMe, 3-SPh-phenyl) | Me | H | H | Single bond | ≥280 (Dichloromethane-methanol) |
| 32 | H | 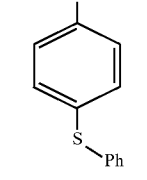 (4-SPh-phenyl) | Ph | H | H | Single bond | 253–255 (Chloroform-methanol-diethyl ether) |
| 33 | 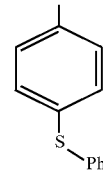 (4-SPh-phenyl) | H |  CH2Cl | H | H | Single bond | 284(Decomp.) (Chloroform-methanol) |
| 34 | 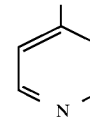 (4-pyridyl) | H | CF3 | H | H | Single bond | ≥300 (Dichloromethane-methanol) |
| 35 | H | H | 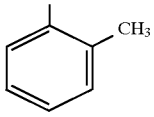 (2-methylphenyl) | H | H | Single bond | NMR(3) |
| 36 | H | H | 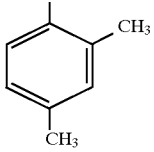 (2,4-dimethylphenyl) | H | H | Single bond | NMR(4) |
| 37 | H | H | 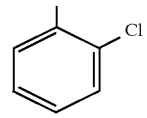 (2-chlorophenyl) | H | H | Single bond | NMR(5) |

TABLE 1-continued

| # | | | Ar/R | | R' | Bond | mp (°C) / solvent |
|---|---|---|---|---|---|---|---|
| 38 | H | H | 3,5-dimethoxyphenyl | H | H | Single bond | NMR(6) |
| 39 | H | H | 3,4,5-trimethoxyphenyl | H | H | Single bond | NMR(7) |
| 40 | H | H | 2-furyl | H | H | Single bond | NMR(8) |
| 41 | H | H | 2-thienyl | H | H | Single bond | NMR(9) |
| 42 | H | H | 5-ethyl-2-thienyl | H | H | Single bond | NMR(10) |
| 43 | H | H | Me | H | Me | Single bond | 123–125 (Diethyl ether) |
| 44 | H | H | n-Bu | H | Me | Single bond | 61–63 (Diethyl ether) |
| 45 | H | H | Me | H | Et | Single bond | 148–150 (Diethyl ether) |
| 46 | H | H | n-Bu | H | Et | Single bond | 76–77 (n-Hexane) |
| 47 | H | H | n-Bu | H | Ph | Single bond | 61–62 (n-Hexane) |
| 48 | H | H | n-Bu | H | 4-methylphenyl | Single bond | 78–80 |
| 49 | H | H | n-Bu | H | 2-pyridyl | Single bond | 46–48 (n-Hexane) |
| 50 | H | H | n-Bu | H | 6-methyl-2-pyridyl | Single bond | 60–62 (n-Hexane) |
| 51 | H | H | n-Bu | H | 6-chloro-2-pyridyl | Single bond | 74–76 (Diethyl ether-n-hexane) |
| 52 | H | H | n-Bu | H | 5-chloro-2-pyridyl | Single bond | 95–97 (Ethyl acetate-n-hexane) |
| 53 | H | H | n-Bu | H | 3-pyridyl | Single bond | 58–60 (Ethyl acetate-n-hexane) |

TABLE 1-continued

| | | | | | | | |
|---|---|---|---|---|---|---|---|
| 54 | H | H | n-Bu | H | 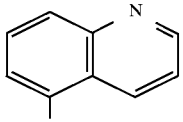 | Single bond | 112–114 (Ethyl acetate-n-hexane) |
| 55 | H | H | n-Bu | H | 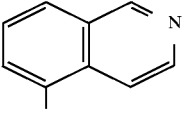 | Single bond | 91–93 (Ethyl acetate-n-hexane) |
| 56 | H | H | n-Bu | H | 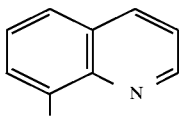 | Single bond | 87–89 (Ethyl acetate-n-hexane) |
| 57 | H | H | n-Bu | H | 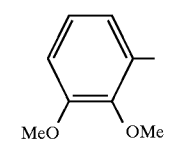 | —CH$_2$— | 95–97 (Ethyl acetate-n-hexane) |
| 58 | H | H | n-Bu | H | 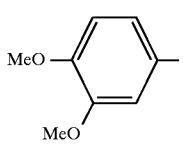 | —CH$_2$— | 95–98 (Diethyl ether-n-hexane) |
| 59 | H | H | n-Bu | H | 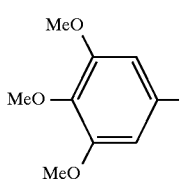 | —CH$_2$— | 100–103 (Ethyl acetate-n-hexane) |
| 60 | Me | H | n-Bu | H | 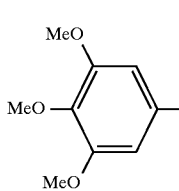 | —CH$_2$— | 113–166 (Diethyl ether-n-hexane) |
| 61 | H | H | Me | H | 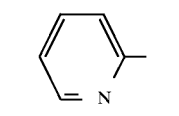 | —CH$_2$— | 144–146(Decomp.) (Dichloromethane-diethyl ether) |
| 62 | H | H | n-Bu | H | 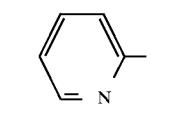 | —CH$_2$— | 70–72 (Diethyl ether-n-hexane) |
| 63 | H | H | Ph | H | 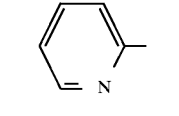 | —CH$_2$— | 135–137(Decomp.) (Dichloromethane-n-hexane) |
| 64 | H | H | n-Bu | H | 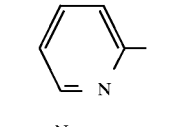 | Me<br>\|<br>—CH— | 61–63 (Diethyl ether-n-hexane) |
| 65 | H | H | n-Bu | H | 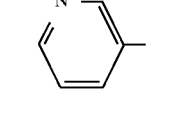 | —CH$_2$— | 136–138(Decomp.) (Dichloromethane-n-hexane) |

TABLE 1-continued

| | | | | | | | |
|---|---|---|---|---|---|---|---|
| 66 | H | H | n-Bu | H | 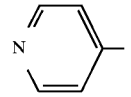 | —CH$_2$— | 177–178 (Decomp.) |
| 67 | Me | H | n-Bu | H | 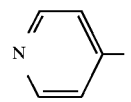 | —CH$_2$— | 126–128 (Ethyl acetate- n-hexane) |
| 68 | H | H | 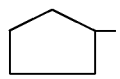 | H | 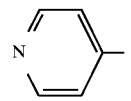 | —CH$_2$— | 138–140 (Dichloro- methane- n-hexane) |
| 69 | H | H |  | H | 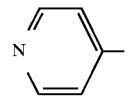 | —CH$_2$— | 141–143 (N,N-dimethyl formamide- water) |
| 70 | H | H | 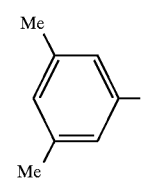 | H | 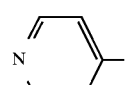 | —CH$_2$— | 145–147 (Ethyl acetate- n-hexane) |
| 71 | H | H | 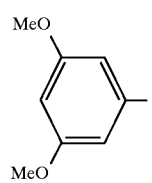 | H | 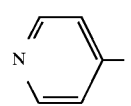 | —CH$_2$— | 172–174 (Ethyl acetate- n-hexane) |
| 72 | H | H | 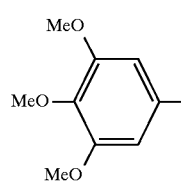 | H | 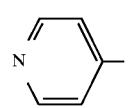 | —CH$_2$— | 180–182 (Ethyl acetate- n-hexane) |
| 73 | H | H |  | H | 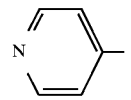 | —CH$_2$— | 110–112 (Ethyl acetate- n-hexane) |
| 74 | H | H | n-Bu | H | 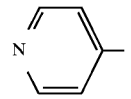 | Me<br>\|<br>—CH— | 60–62 (Diethyl ether-n-hexane) |
| 75 | H | H | n-Bu | H | 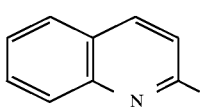 | —CH$_2$— | 75–77 (Diethyl ether-n-hexane) |
| 76 | H | H | n-Bu | H | 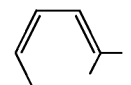 | —C$_3$H$_6$— | 55–58 (Diethyl ether- n-hexane) |
| 77 | H | Br | n-Bu | H | 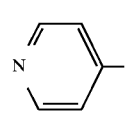 | —CH$_2$— | 157–159 (1,2-Di- methoxy ethane-water) |
| 78 | Ph | H | CH$_3$ | 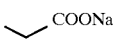COONa | Na | Single bond | ≧280 |

TABLE 1-continued

| 79 | H | 4-(PhS)-C6H4- | cyclohexyl | | H | Single bond | 271–272 (Chloroform-methanol-diethyl ether) |

[Structure: pyrazolo-pyridazinone core with R¹, R², R³, R⁴, R⁶ substituents]

| No. | R¹ | R² | R³ | R⁴ | R⁶ | Melting point (°C.) (Recrystallization solvent) |
|-----|----|----|----|----|----|-------------------------------------------------|
| 80 | Ph | H | cyclopentyl | | Et | 258–260 (Dichloromethane-hexane) |
| 81 | H | H | H | H | 4-(PhS)-C6H4-CH2CH2- | 155–157 |
| 82 | 1-methyl-pyrrol-2-yl | H | Me | H | —COOCH₃ | 168–170 |
| 83 | 1-methyl-pyrrol-2-yl | H | H | H | —(CH2)6—C(O)N(Me)2 | 86–87 |
| 84 | 1-methyl-pyrrol-2-yl | H | H | H | —(CH2)3—C(O)-piperidinyl | 90–92 |
| 85 | H | H | OH | CN | Et | ≧280 |
| 86 | 4-pyridyl | H | H | H | —CH2—C≡CH | 224–230 (Chloroform-diethyl ether) |
| 87 | H | H | —C(NH2)=N—N(CH3)— | | Et | NMR(11) |

TABLE 1-continued

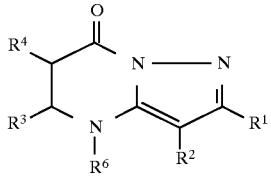

| No. | R¹ | R² | R³ | R⁴ | R⁶ | Melting point (°C.) (Recrystallization solvent) |
|---|---|---|---|---|---|---|
| 88 | 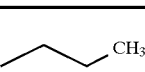 | H | ~~~CH₃ | CN | H | 140–142 (Ether-hexane) |
| 89 | H | H | 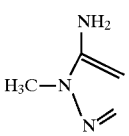 | | Et | NMR(12) |

| No. | | NMR (δ:ppm) |
|---|---|---|
| 11 | NMR(1) CDCl₃ | 1.31(3H, s), 2.12(2H, t, J=7.4), 2.84(2H, t, J=7.4), 3.95(4H, m), 6.17(1H, d, J=2.0), 7.82(1H, d, J=2.0) |
| 14 | NMR(2) CDCl₃ | 1.24(3H, t, J=6.9), 3.60(2H, t, J=6.9), 4.50(2H, s), 5.81(1H, s), 6.15(1H, d, J=2.0), 7.81(1H, d, J=2.0) |
| 35 | NMR(3) DMSO-d₆ | 2.34(3H, s), 5.68(1H, s), 6.15(1H, d, J=2.0), 7.3–7.5(4H, m), 7.90(1H, d, J=2.0), 12.3–12.7(1H, brs) |
| 36 | NMR(4) DMSO-d₆ | 2.37(3H, s), 2.42(3H, s), 5.72(1H, s), 6.22(1H, d, J=2.0), 7.2–7.3(2H, m), 7.41(1H, d, J=7.4), 7.97(1H, d, J=2.0), 12.3–12.9(1H, brs) |
| 37 | NMR(5) DMSO-d₆ | 5.77(1H, s), 6.20(1H, d, J=2.0), 7.5–7.8(4H, m), 7.94(1H, d, J=2.0), 12.6–13.0(1H, brs) |
| 38 | NMR(6) DMSO-d₆ | 3.85(6H, s), 6.13(1H, s), 6.22(1H, d, J=2.0), 6.72(1H, s), 6.98(2H, s), 7.91(1H, d, J=2.0), 12.3–12.6(1H, brs) |
| 39 | NMR(7) DMSO-d₆ | 3.74(3H, s), 3.90(6H, s), 6.19 (1H, s), 6.23(1H, s), 7.14(2H, s), 7.91(1H, s), 12.2–12.5(1H, brs) |
| 40 | NMR(8) DMSO-d₆ | 6.19(1H, s), 6.28(1H, d, J=2.0), 6.87(1H, dd, J=1.5, 4.0), 7.53(1H, d, J=4.0), 7.95(1H, d, J=2.0), 8.12(1h, d, J=1.5), 12.1–13.3(1H, brs) |
| 41 | NMR(9) DMSO-d₆ | 6.09(1H, s), 6.29(1H, d, J=2.0), 7.37(1H, t, J=4.0), 7.97(3H, m), 12.3–13.0(1H, brs) |
| 42 | NMR(10) DMSO-d₆ | 4.15(2H, s), 5.62(1H, s), 6.14(1H, d, J=2.0), 7.0–7.1(2H, m), 7.45(1H, d, J=5.0), 7.85(1H, d, J=2.0), 12.1–12.8(1H, brs) |
| 87 | NMR(11) DMSO-d₆ | 1.20(3H, t, J=6.9), 3.25(3H, s), 4.63(2H, q, J=6.9), 4.98(2H, s), 6.20(1H, d, J=3.5), 8.29(1H, d, J=3.5) |
| 89 | NMR(12) DMSO-d₆ | 1.11(3H, t, J=6.9), 3.56(3H, s), 4.63(2H, q, J=6.9), 5.32(2H, s), 6.28(1H, d, J=3.5), 8.23(1H, d, J=3.5) |

Pharmacological Test Example 1

Using 6-week-old male Sprague-Dawley rats (n=7/group), the pain threshold of each rat's left hind paw was determined using Analgesy-Meter (Unicom) in accordance with the Randall-Sellitto method [Randall, L. O. and Sellitto, J. J., Arch. Int. Pharmacodyn., 111, 409 (1957)]. The value thus obtained was termed "pre-value".

One hour after the measurement of pre-value, 0.1 ml of a 20% yeast suspension was subcutaneously injected into the left hind paw of each rat. Immediately after the yeast injection, a 5% gum arabic suspension containing the compound of the invention was orally administered to the rats of the test group in an amount of 10 ml/kg, whereas a 5% gum arabic suspension (not containing the compound of the invention) was administered likewise to the rats of the control group.

The pain threshold of each rat's left hind paw was determined in the same manner as above at an interval of exactly one hour from the time of the yeast injection. The value thus obtained was termed "post-value".

The recovery rate of the pain threshold was calculated from post-values and pre-values of the rats in each group, by means of the following formula.

$$\text{Recovery rate of pain threshold (\%)} = \frac{\text{(Test group average post-value)} - \text{(Control group average post-value)}}{\text{(Control group average pre-value)} - \text{(Control group average post-value)}} \times 100$$

The results (the highest recovery rate) are shown in Table 2.

TABLE 2

| Production Example No. | Dosage (mg/kg) | Recovery rate (%) | Time from yeast injection (hour later) |
|---|---|---|---|
| 62 | 3 | 86.6 | 3 |
| 63 | 3 | 69.0 | 1 |
| 65 | 3 | 95.3 | 3 |
| 66 | 3 | 92.8 | 4 |
| 67 | 3 | 65.9 | 4 |

Pharmacological Test Example 2

Using 6-week-old male Sprague-Dawley rats (n=7/group, the pain threshold of each rat's left hind paw was determined using Analgesy-Meter (Unicom) in accordance with the Randall-Sellitto method [Randall, L. O. and Sellitto J. J., Arch. Int. Pharmacodyn., 111, 409 (1957)]. thus obtained was termed "pre-value".

One hour after the measurement of pre-value, a 5% gum arabic suspension containing the compound of the invention was orally administered to the rats of the test group in an amount of 10 ml/kg so that the dosage of the compound of the invention was 1 mg/kg, whereas a 5% gum arabic suspension (not containing the compound of the invention) was administered likewise to the rats of the control group. One hour later, an aqueous physiological saline solution containing substance P (25 ng/0.1 ml) was subcutaneously injected into the left hind paw of each rat.

The pain threshold of each rat's left hind paw was determined in the same manner as above at a predetermined interval from the time of the substance P injection. The value thus obtained was termed "post-value".

The recovery rate of the pain threshold (%) was calculated from post-values and pre-values of the rats in each group, by means of the following formula.

$$\text{Recovery rate of pain threshold (\%)} = \frac{\text{(Test group average post-value)} - \text{(Control group average post-value)}}{\text{(Control group average pre-value)} - \text{(Control group average post-value)}} \times 100$$

The results (the highest recovery rate) are shown in Table 3.

TABLE 3

| Production Example No. | Recovery rate (%) | Time from substance P injection (minutes later) |
|---|---|---|
| 1* | 50.8 | 15 |
| 46* | 77.5 | 15 |
| 49 | 56.2 | 60 |
| 50 | 51.5 | 60 |
| 51 | 75.3 | 60 |
| 52 | 64.3 | 30 |
| 53 | 50.4 | 30 |
| 54 | 54.6 | 15 |
| 55 | 62.0 | 15 |
| 57 | 61.0 | 60 |
| 58 | 90.7 | 30 |
| 59 | 65.3 | 60 |
| 60 | 41.0 | 30 |
| 62 | 106.7 | 60 |
| 63 | 84.6 | 60 |
| 64 | 72.2 | 15 |
| 65 | 76.9 | 60 |
| 66 | 94.9 | 15 |
| 67 | 67.5 | 30 |
| 69 | 87.4 | 60 |
| 73 | 85.5 | 30 |
| 74 | 53.2 | 30 |
| 75 | 50.4 | 30 |
| 76 | 72.4 | 60 |

*Dosage = 3 mg/g

Pharmacological Test Example 3

The same procedure as in Pharmacological Test Example 2 was followed except that compounds obtained in Production Examples 12, 18 and 28 were administered in an amount of 10 mg/kg. The results are shown in Table 4.

TABLE 4

| Production Example No. | Recovery rate (%) | Time from substance P injection (minutes later) |
|---|---|---|
| 12 | 26.1 | 15 |
| 18 | 37.3 | 60 |
| 28 | 26.6 | 30 |

Given below are Formulation Examples for manufacturing analgesic compositions of the invention.

Formulation Example 1
Manufacture of tablets

Tablets (1000 tables) for oral administration, each containing 5 mg of the compound obtained in Production Example 66, were manufactured according to the following formula:

| | |
|---|---|
| Compound of Production Example 66 | 5 g |
| Lactose (product of Japanese pharmacopoeia: JP) | 50 g |
| Corn starch (JP) | 25 g |
| Crystalline cellulose (JP) | 25 g |
| Methyl cellulose (JP) | 1.5 g |
| Magnesium stearate (JP) | 1 g |

More specifically, the compound of Production Example 66, lactose, corn starch and crystalline cellulose were fully blended and granulated using a 5% aqueous solution of methyl cellulose. The granulated mixture was passed through a 200-mesh sieve and dried carefully. The dried granules were passed through a 200-mesh sieve, and the granules under the sieve were mixed with magnesium stearate and compression-molded into tablets.

Formulation Example 2
Manufacture of capsules

Two-piece hard gelatin capsules (1000 units) for oral administration, each containing 10 mg of the compound obtained in Production Example 1 were manufactured according to the following formula:

| | |
|---|---|
| Compound of Production Example 1 | 10 g |
| Lactose (JP) | 80 g |
| Corn starch (JP) | 30 g |
| Talc (JP) | 5 g |
| Magnesium stearate (JP) | 1 g |

More specifically, the ingredients according to the above formula were finely pulverized and blended to give a homogeneous composition. This composition was filled into proper-sized gelatin capsule shells for oral administration.

Formulation Example 3
Manufacture of injectable form

An aqueous solution for non-oral administration, containing the compound obtained in Production Example 66 and sterilized, was manufactured according to the following formula:

| | |
|---|---|
| Compound of Production Example 66 | 1 g |
| Polyethylene glycol (JP) (molecular weight: 4000) | 0.9 g |
| Sodium chloride (JP) | 0.9 g |
| Polyoxyethylene sorbitan monooleate (JP) | 0.4 g |
| Sodium metabisulfite (JP) | 0.1 g |
| Methylparaben (JP) | 0.18 g |
| Propylparaben (JP) | 0.02 g |
| Distilled water for injection | 100 ml |

More specifically, the above parabens, sodium metabisulfite and sodium chloride were dissolved in about half the amount of the distilled water while being stirred at 80° C. The solution was cooled to 40° C. The compound of Production Example 66 and polyoxyethylene sorbitan monooleate were dissolved therein. The remaining distilled water for injection was added to the solution to make a final volume for injection, followed by sterilization by filtrating through a suitable filter paper to provide an injectable form of the compound.

What is claimed is:

1. An analgesic composition comprising as an active ingredient at least one compound selected from the group consisting of:
pyrazolo[1,5-a]pyrimidine derivatives of formula (1):

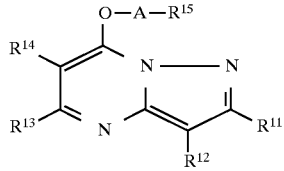

wherein $R^{11}$ represents hydrogen, lower alkyl, or phenyl optionally having lower alkyl or phenylthio as a substituent, $R^{12}$ represents hydrogen, halogen, phenyl, phenyl having halogen, phenylthio or trifluoromethyl as a substituent, phenyl having trifluoromethyl and nitro as substituents, or phenyl having lower alkoxy and phenylthio as substituents, $R^{13}$ represents hydrogen, lower alkyl optionally having oxo, ethylenedioxy, lower alkanoyloxy, lower alkoxy, lower alkylthio, carboxyl, halogen or thienyl as a substituent, lower alkenyl, cycloalkyl, or phenyl optionally having 1 to 3 substituents selected from the group consisting of lower alkyl, halogen and lower alkoxy, furyl or thienyl, $R^{14}$ represents hydrogen, carboxyl, lower alkoxycarbonyl, nitro, halogen, or lower alkyl having lower alkoxycarbonyl or the residue of an alkali metal salt of carboxylic acid as a substituent; $R^{13}$ and $R^{14}$ may conjointly form lower alkylene, $R^{15}$ represents hydrogen, alkali metal, lower alkyl, phenyl optionally having 1 to 3 substituents selected from the group consisting of lower alkyl and lower alkoxy, pyridyl optionally having lower alkyl or halogen as a substituent, quinolyl or isoquinolyl, and A represents a single bond or lower alkylene, with the proviso that the following compounds are excluded from formula (1):
   (A) when $R^{11}$ is hydrogen, $R^{12}$ is phenyl or phenyl having one or more substituents as defined, $R^{13}$ is hydrogen, $R^{14}$ is hydrogen, A is a single bond, and $R^{15}$ is hydrogen or alkali metal, and
   (B) when $R^{11}$ is hydrogen, $R^{12}$ is hydrogen or halogen, $R^{13}$ is hydrogen, lower alkyl or phenl, $R^{14}$ is hydrogen or lower alkoxycarbonyl, and —A—$R^{15}$ is defined as hydrogen or lower alkyl;
4,7-dihydropyrazolo[1,5-a]pyrimidine derivatives of formula (2):

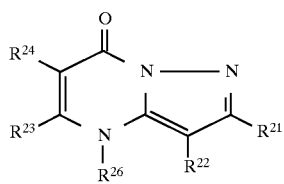

wherein $R^{21}$ represents hydrogen or phenyl, $R^{22}$ represents hydrogen, $R^{23}$ represents hydrogen, lower alkyl or hydroxyl, $R^{24}$ represents hydrogen or cyano, $R^{23}$ and $R^{24}$ may conjointly form lower alkylene or —C(NH$_2$)=N—N(CH$_3$)—, $R^{26}$ represents lower alkyl, lower alkoxycarbonyl, 4-phenylthiobenzyl, 2-propynyl, 2-piperidinocarbonylethyl or 5-dimethylaminocarbonylpentyl, provided that when $R^{26}$ is lower alkyl, then $R^{24}$ is cyano or $R^{23}$ and $R^{24}$ conjointly form lower alkylene or —C(NH$_2$)=N—N (CH$_3$)—; and 4,5,6,7-tetrahydropyrazolo[1,5-a] pyrimidine derivatives of formula (3):

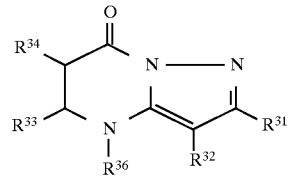

wherein $R^{31}$ represents hydrogen or N-(lower) alkylpyrrolyl, $R^{32}$ represents hydrogen, $R^{33}$ represents lower alkyl, $R^{34}$ represents cyano, $R^{33}$ and $R^{34}$ may conjointly form =C(NH$_2$)—N(CH$_3$)—N=, and $R^{36}$ represents hydrogen or lower alkyl; and also comprising a pharmaceutically acceptable non-toxic carrier.

2. An analgesic composition comprising as an active ingredient at least one pyrazolo[1,5-a]pyrimidine derivative of formula (1):

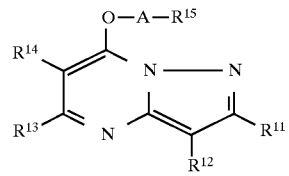

wherein $R^{11}$ represents lower alkyl, $R^{12}$ and $R^{14}$ represent hydrogen, $R^{13}$ represents lower alkyl, $R^{15}$ represents pyridyl or phenyl having 3 lower alkoxy groups as substituents and A represents methylene, or wherein $R^{12}$ represents halogen, $R^{11}$ and $R^{14}$ represent hydrogen, $R^{13}$ represents lower alkyl, $R^{15}$ represents pyridyl and A represents methylene; and also comprising a pharmaceutically acceptable non-toxic carrier.

3. An analgesic composition according to claim 2 which comprises as the active ingredient at least one compound of formula (1) wherein $R^{12}$ represents hydrogen.

4. An analgesic composition comprising as an active ingredient at least one pyrazolo[1,5-a]pyrimidine derivative of formula (1) of claim 1 wherein $R^{12}$ represents hydrogen, which derivative is selected from the group consisting of:
   1) compounds wherein $R^{11}$ represents lower alkyl, $R^{13}$ represents n-butyl, $R^{14}$ represents hydrogen, $R^{15}$ represents pyridyl or phenyl having 3 lower alkoxy groups as substituents and A represents methylene;
   2) compounds wherein $R^{11}$ represents hydrogen, $R^{13}$ and $R^{14}$ conjointly form tetramethylene, $R^{15}$ represents pyridyl and A represents methylene;
   3) compounds wherein $R^{11}$ and $R^{14}$ represent hydrogen, $R^{13}$ represents cycloalkyl, (lower) alkoxy (lower) alkyl, (lower) alkylthio (lower) alkyl or phenyl, $R^{15}$ represents pyridyl and A represents methylene;
   4) compounds wherein $R^{11}$ and $R^{14}$ represent hydrogen, $R^{13}$ represents n-butyl, $R^{15}$ represents pyridyl optionally having lower alkyl or halogen as a substituent, quinolyl or isoquinolyl and A represents a single bond; and
   5) compounds wherein $R^{11}$ and $R^{14}$ represent hydrogen, $R^{13}$ represents n-butyl, $R^{15}$ represents phenyl having 2 or 3 lower alkoxy groups as substituents, pyridyl or quinolyl and A represents lower alkylene; and also comprising a pharmaceutically acceptable non-toxic carrier.

5. An analgesic composition according to claim 4 which comprises as the active ingredient at least one pyrazolo[1, 5-a]pyrimidine derivative of formula (1) selected from the group consisting of:
- [1] compounds wherein R represents lower alkyl, $R^{13}$ represents n-butyl, $R^{14}$ represents hydrogen, $R^{15}$ represents pyridyl and A represents methylene;
- [2] compounds wherein R represents hydrogen, $R^{13}$ and $R^{14}$ conjointly form tetramethylene, $R^{15}$ represents pyridyl and A represents methylene;
- [3] compounds wherein $R^{11}$ and $R^{14}$ represent hydrogen, $R^{13}$ represents cyclohexyl or phenyl, $R^{15}$ represents pyridyl and A represents methylene;
- [4] compounds wherein $R^{11}$ and $R^{14}$ represent hydrogen, $R^{13}$ represents n-butyl, $R^{15}$ represents halogen-substituted pyridyl or isoquinolyl and A represents a single bond; and
- [5] compounds wherein $R^{11}$ and $R^{14}$ represent hydrogen, $R^{13}$ represents n-butyl, $R^{15}$ represents phenyl having 2 or 3 lower alkoxy groups as substituents or pyridyl and A represents lower alkylene.

6. An analgesic composition according to claim 4 which comprises as the active ingredient at least one pyrazolo[1,5-a]pyrimidine derivative of formula (1) wherein $R^{11}$ and $R^{14}$ represent hydrogen, $R^{13}$ represents n-butyl, $R^{15}$ represents pyridyl and A represents a single bond or lower alkylene.

7. An analgesic composition according to claim 6 wherein the active ingredient is 5-n-butyl-7-(4-pyridylmethoxy)pyrazolo[1,5-a]pyrimidine.

8. A method for treating pain comprising administering to a patient in need thereof an effective amount of an analgesic composition comprising as an active ingredient at least one compound selected from the group consisting of:
pyrazolo[1,5-a]pyrimidine derivatives of formula (1):

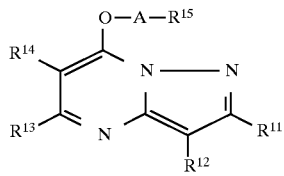

wherein $R^{11}$ represents hydrogen, lower alkyl, or phenyl optionally having lower alkyl or phenylthio as a substituent, $R^{12}$ represents hydrogen, halogen, phenyl, phenyl having halogen, phenylthio or trifluoromethyl as a substituent, phenyl having trifluoromethyl and nitro as substituents, or phenyl having lower alkoxy and phenylthio as substituents, $R^{13}$ represents hydrogen, lower alkyl optionally having oxo, ethylenedioxy, lower alkanoyloxy, lower alkoxy, lower alkylthio, carboxyl, halogen or thienyl as a substituent, lower alkenyl, cycloalkyl, or phenyl optionally having 1 to 3 substituents selected from the group consisting of lower alkyl, halogen and lower alkoxy, furyl or thienyl, $R^{14}$ represents hydrogen, carboxyl, lower alkoxycarbonyl, nitro, halogen, or lower alkyl having lower alkoxycarbonyl or the residue of an alkali metal salt of carboxylic acid as a substituent; $R^{13}$ and $R^{14}$ may conjointly form lower alkylene, $R^{15}$ represents hydrogen, alkali metal, lower alkyl, phenyl optionally having 1 to 3 substituents selected from the group consisting of lower alkyl and lower alkoxy, pyridyl optionally having lower alkyl or halogen as a substituent, quinolyl or isoquinolyl, and A represents a single bond or lower alkylene;

4,7-dihydropyrazolo[1,5-a]pyrimidine derivatives of formula (2):

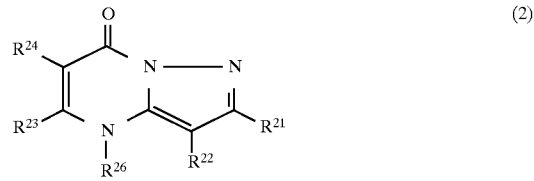

wherein $R^{21}$ represents hydrogen or phenyl, $R^{22}$ represents hydrogen, $R^{23}$ represents hydrogen, lower alkyl or hydroxyl, $R^{24}$ represents hydrogen or cyano, $R^{23}$ and $R^{24}$ may conjointly form lower alkylene or —C(NH$_2$)=N—N(CH$_3$)—, $R^{26}$ represents lower alkyl, lower alkoxycarbonyl, 4-phenylthiobenzyl, 2-propynyl, 2-piperidinocarbonylethyl or 5-dimethylaminocarbonylpentyl, provided that when $R^{26}$ is lower alkyl, then $R^{24}$ is cyano or $R^{23}$ and $R^{24}$ conjointly form lower alkylene or —C(NH$_2$)=N—N(CH$_3$)—; and 4,5,6,7-tetrahydropyrazolo[1,5-a]pyrimidine derivatives of formula (3):

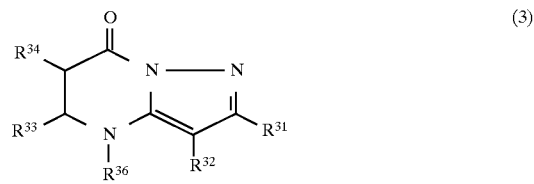

wherein $R^{31}$ represents hydrogen or N-(lower)alkylpyrrolyl, $R^{32}$ represents hydrogen, $R^{33}$ represents lower alkyl, $R^{34}$ represents cyano, $R^{33}$ and $R^{34}$ may conjointly form =C(NH$_2$)—N(CH$_3$)—N=, and $R^{36}$ represents hydrogen or lower alkyl; and also comprising a pharmaceutically acceptable non-toxic carrier.

9. A method of claim 8, wherein said pain is selected from the group consisting of post-operative pain, migraine, pain associated with gout, neurogenic pain, cancerous pain and chronic pain.

10. A method for treating pain comprising administering to a patient in need thereof an effective amount of at least one compound selected from the group consisting of:
pyrazolo[1,5-a]pyrimidine derivatives of formula (1):

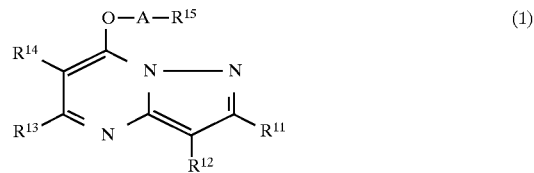

wherein $R^{11}$ represents hydrogen, lower alkyl, or phenyl optionally having lower alkyl or phenylthio as a substituent, $R^{12}$ represents hydrogen, halogen, phenyl, phenyl having halogen, phenylthio or trifluoromethyl as a substituent, phenyl having trifluoromethyl and nitro as substituents, or phenyl having lower alkoxy and phenylthio as substituents, $R^{13}$ represents hydrogen, lower alkyl optionally having oxo, ethylenedioxy, lower alkanoyloxy, lower alkoxy, lower alkylthio, carboxyl, halogen or thienyl as a substituent, lower alkenyl, cycloalkyl, or phenyl optionally having 1 to 3 substituents selected from the group consisting of lower alkyl, halogen and lower alkoxy, furyl or thienyl, $R^{14}$ represents hydrogen, carboxyl, lower alkoxycarbonyl, nitro, halogen, or lower alkyl having lower alkoxycarbonyl or the residue of an alkali metal salt of carboxylic acid as a substituent; $R^{13}$ and $R^{14}$ may conjointly form lower alkylene, $R^{15}$ represents hydrogen, alkali metal, lower alkyl, phenyl optionally having 1 to 3 substituents selected from the group consisting of lower alkyl and lower alkoxy, pyridyl optionally having lower alkyl or halogen as a substituent, quinolyl or isoquinolyl, and A represents a single bond or lower alkylene;

4,7-dihydropyrazolo[1,5-a]pyrimidine derivatives of formula (2):

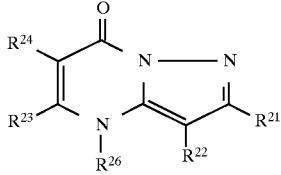

(2)

wherein $R^{21}$ represents hydrogen or phenyl, $R^{22}$ represents hydrogen, $R^{23}$ represents hydrogen, lower alkyl or hydroxyl, $R^{24}$ represents hydrogen or cyano, $R^{23}$ and $R^{24}$ may conjointly form lower alkylene or —C(NH$_2$)=N—N(CH$_3$)—, $R^{26}$ represents lower alkyl, lower alkoxycarbonyl, 4-phenylthiobenzyl, 2-propynyl, 2-piperidinocarbonylethyl or 5-dimethylaminocarbonylpentyl, provided that when $R^{26}$ is lower alkyl, then $R^{24}$ is cyano or $R^{23}$ and $R^{24}$ conjointly form lower alkylene or —C(NH$_2$)=N—N(CH$_3$)—; and 4,5,6,7-tetrahydropyrazolo[1,5-a]pyrimidine derivatives of formula (3):

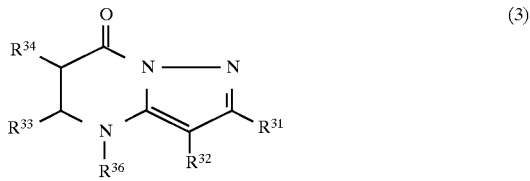

(3)

wherein $R^{31}$ represents hydrogen or N-(lower)alkylpyrrolyl, $R^{32}$ represents hydrogen, $R^{33}$ represents lower alkyl, $R^{34}$ represents cyano, $R^{33}$ and $R^{34}$ may conjointly form =C(NH$_2$)—N(CH$_3$)—N=, and $R^{36}$ represents hydrogen or lower alkyl.

11. A method of claim 10, wherein said pain is selected from the group consisting of post-operative pain, migraine, pain associated with gout, neurogenic pain, cancerous pain and chronic pain.

* * * * *